(12) United States Patent
Miura et al.

(10) Patent No.: US 7,285,684 B2
(45) Date of Patent: Oct. 23, 2007

(54) PROCESS FOR SEPARATING IMIDE COMPOUNDS

(75) Inventors: Hiroyuki Miura, Takasago (JP); Hitoshi Watanabe, Himeji (JP); Akihiro Kuwana, Himeji (JP); Mami Shimamura, Himeji (JP); Naruhisa Hirai, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/980,588

(22) PCT Filed: Mar. 30, 2001

(86) PCT No.: PCT/JP01/02844

§ 371 (c)(1),
(2), (4) Date: Aug. 10, 2006

(87) PCT Pub. No.: WO01/74487

PCT Pub. Date: Oct. 11, 2001

(65) Prior Publication Data

US 2002/0169331 A1 Nov. 14, 2002

(30) Foreign Application Priority Data

Apr. 4, 2000 (JP) ............................ 2000-102795
Apr. 4, 2000 (JP) ............................ 2000-102796

(51) Int. Cl.
*C07C 45/27* (2006.01)
(52) U.S. Cl. ...................... 568/343; 568/344; 568/357; 568/366
(58) Field of Classification Search ................ 568/344, 568/343, 357, 366
See application file for complete search history.

(56) References Cited

U.S. PATENT DOCUMENTS 5,030,739 A 7/1991 Foricher et al.

FOREIGN PATENT DOCUMENTS

| JP | 63-005076 A | 1/1988 |
| JP | 8-038909 A | 2/1996 |
| JP | 9-278675 A | 10/1997 |
| JP | 9-327626 A | 12/1997 |
| JP | 10-114702 A | 5/1998 |
| JP | 10-316610 A | 12/1998 |
| JP | 11-188265 A | 7/1999 |
| JP | 11-239730 A | 9/1999 |
| WO | 99/41219 | 8/1999 |
| WO | 99/50204 | 10/1999 |

OTHER PUBLICATIONS

An English translation of JP 8-38909 A, Ishii et al. (Feb. 13, 2006), Japan.*
A New Synthetic Method of Hydroxy Lactones Using N-Hydroxyphthalimide via Radical Coupling Reaction; The 76th Spring Annual Meeting of Chemical Society of Japan; 1999; p. 998-1000.

* cited by examiner

*Primary Examiner*—Rebecca Anderson
(74) *Attorney, Agent, or Firm*—Birch, Stewart, Kolasch & Birch, LLP

(57) ABSTRACT

A reaction mixture obtained by reacting a substrate in the presence of an imide compound having an imide unit represented by the formula (1) can be efficiently separated through crystallization and/or extraction with a specific solvent into the imide compound and a reaction product. (In the formula, X represents oxygen, hydroxyl, or acyloxy.) Furthermore, a mixture comprising the imide compound and a metal catalyst can be efficiently separated through crystallization, adsorption, and/or extraction into the imide compound and the metal catalyst.

4 Claims, 1 Drawing Sheet

PROCESS FOR SEPARATING IMIDE COMPOUNDS

This application is the national phase under 35 U.S.C. § 371 of PCT International Application No. PCT/JP01/02844 which has an International filing date of Mar. 30, 2001, which designated the United States of America.

TECHNICAL FIELD

This invention relates to a process for separating, from a reaction mixture obtained by reacting a substrate in the presence of the specific imide compound, a reaction product and the imide compound, a process for separating the imide compound and a metal catalyst, and a process for regenerating the imide compound which has been used in a reaction to be deactivated.

BACKGROUND ART

By utilizing an imide compound such as N-hydroxyphthalimide and N-acetoxyphthalimide, a variety of reactions (e.g., oxidation with molecular oxygen, carboxylation, nitration, sulfonation, acylation, radical-coupling reaction) can be smoothly carried out under a mild condition.

For example, Japanese Patent Application Laid-Open No. 38909/1996 (JP-A-8-38909) and Japanese Patent Application Laid-Open No. 327626/1997 (JP-A-9-327626) disclose a process for oxidizing a substrate (e.g., a hydrocarbon, an alcohol) with a molecular oxygen in the presence of an imide compound such as N-hydroxyphthalimide, and if necessary, a metal co-catalyst to produce an alcohol, an aldehyde, a ketone, and a carboxylic acid corresponding to the substrate.

Moreover, Japanese Patent Application Laid-Open No. 278675/1997 (JP-A-9-278675) discloses a process for oxidizing a conjugate compound with the imide compound.

Japanese Patent Application Laid-Open No. 316610/1998 (JP-A-10-316610) discloses a process for oxidizing an ether in the presence of the imide compound to produce an ester, an acid anhydride, a lactone or the like. WO99/50204 discloses a process for oxidizing a compound having a non-aromatic ethylene bond with a molecular oxygen in the presence of the imide compound and a co-oxidizing agent to produce the corresponding epoxide, and a process for oxidizing a ketone with a molecular oxygen in the presence of the imide compound and a co-oxidizing agent to produce the corresponding ester or lactone.

Further, Japanese Patent Application Laid-Open No. 239730/1999 (JP-A-11-239730) discloses a process for reacting a substrate with a nitrogen oxide in the presence of the imide compound to obtain the corresponding nitro compound, and a process for reacting a substrate with carbon monoxide and oxygen in the presence of the imide compound to produce the corresponding carboxylic acid. WO99/41219 discloses that an acylation reaction proceeds under a mild condition by reacting a substrate with oxygen and a vicinal (adjacent) dicarbonyl compound (e.g., biacetyl) in the presence of the imide compound. Furthermore, the Lecture Draft of Spring Annual Meeting of Chemical Society of Japan (1999) reports that an $\alpha$, $\beta$-unsaturated ester and an alcohol are reacted with oxygen in the presence of N-hydroxyphthalimide as a catalyst, thereby a radical-coupling reaction proceeds to form $\alpha$-hydroxy-$\gamma$-butyrolactone with high yield. Moreover, the literature reports that a hydrocarbon such as an adamantane is reacted with oxygen and sulfur dioxide by using N-hydroxyphthalimide as a catalyst to form the corresponding sulfonic acid.

As mentioned above, the imide compound has been utilized as a catalyst for a wide variety of organic synthetic reactions. After utilizing the imide compound for a variety of reactions, there is proposed a process for separating a reaction product and the imide compound. For example, Japanese Patent Application Laid-Open No. 114702/1998 (JP-A-10-114702) discloses a process for separating a reaction product and an imide compound from a reaction mixture obtained by oxidizing a substrate in the presence of an oxidation catalyst (the imide compound). In this process, an aqueous solvent and a non-water-soluble solvent separable from the aqueous solvent are used to distribute the oxidation reaction product into a phase of the aqueous solvent and the imide catalyst into a phase of the non-water-soluble solvent, respectively. Therefore, the process is suitable for separating a water-soluble reaction product and a non-water-soluble catalyst, but it is difficult to separate a low-polar or non-water-soluble reaction product and a non-water-soluble catalyst. Further, in the process, it is sometimes difficult to separate a water-soluble product from an aqueous phase depending on the species of the oxidation reaction product. In particular, when a reaction is carried out in the coexistence of a metal catalyst in order to accelerate the reaction, it is difficult to separate the oxidation catalyst and the metal catalyst efficiently, as well as separating the reaction product. Therefore, it is difficult to separate, recover and reuse the metal catalyst.

Moreover, when the imide compound is utilized as a catalyst for various reactions, as the reaction proceeds, the imide compound changes into the corresponding N-non-substituted imide compound or N-substituted oxyimide compound in which a substrate is attached to oxygen atom adjacent to nitrogen atom (e.g., N-alkoxyimide compound) to deteriorate an catalytic activity considerably. In the case where such a catalyst which has been deactivated (hereinafter, sometimes referred to a deactivated catalyst) contaminates an article of the reaction product, there is a possibility that the quality of the article is deteriorated.

Further, a desired result cannot be arrived even when the deactivated catalyst is recycled to the reaction system without the specific treatment. Thus, as a method for regenerating the catalyst which has been deactivated, Japanese Patent Application Laid-Open No. 188265/1999 (JP-A-11-188265) discloses a process for treating the deactivated imide compound with a hydroxylamine or an acid. However, the process cannot still provide a satisfied regeneration yield of the imide-series catalyst.

It is, therefore, an object of the present invention to provide a process for efficiently separating a reaction product and an imide compound from the reaction mixture.

It is another object of the invention to provide a process for conveniently obtaining a reaction product with high purity.

A further object of the invention is to provide a process for efficiently separating an imide compound and a metal catalyst from a mixture containing the imide compound and the metal catalyst.

It is yet another object of the invention to provide a process for efficiently regenerating an imide compound which has been utilized in a reaction to be deactivated by a simple and convenient operation.

DISCLOSURE OF THE INVENTION

The present inventors did much investigation to accomplish the above objects, and as a result, found that an imide compound and a reaction product can be efficiently separated by a crystallization operation and/or an extraction operation with a specific solvent, and that an imide compound and a metal catalyst can be efficiently separated by a crystallization, an adsorption and/or an extraction operations. The present invention has been accomplished based on the above findings.

Thus, a process of the present invention can realize the separation of a reaction product and an imide compound from a reaction mixture obtained by reacting a substrate in the presence of the imide compound having an imide unit represented by the following formula (1):

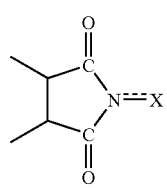

(1)

wherein X represents an oxygen atom, a hydroxyl group or an acyloxy group, by (A1) a solvent-crystallization step for crystallizing the imide compound with at least one solvent selected from the group consisting of a hydrocarbon, a chain ether and water, (A2) a cooling-crystallization step for crystallizing the reaction product by cooling, or (B) an extraction step for distributing the reaction product into a phase of a water-insoluble solvent (or non-water-soluble solvent) and the imide compound into a phase of an aqueous solvent, respectively by using the aqueous solvent containing at least water and the water-insoluble solvent separable from the aqueous solvent.

In the solvent-crystallization step (A1), the hydrocarbon may be an aliphatic hydrocarbon having 4 to 16 carbon atoms or an alicyclic hydrocarbon having 4 to 16 carbon atoms, and the chain ether may be a $diC_{1-6}$alkyl ether or a $C_{1-6}$alkyl $C_{6-10}$aryl ether. The reaction product may be a compound soluble in the solvent for crystallization (e.g., an oxidation reaction product of an alicyclic hydrocarbon or an alicyclic alcohol).

In the cooling-crystallization step (A2), a solvent which is a poor solvent for the reaction product and is a good solvent for the imide compound (e.g., a carboxylic acid and/or a hydrocarbon) may be used as a reaction solvent. The reaction product may be an oxidation reaction product of an alicyclic hydrocarbon or a methyl group-containing aromatic compound (in particular, an aliphatic carboxylic acid having 6 or more carbon atoms, or an aromatic carboxylic acid).

In the extraction step (B), the aqueous solvent may be water and may contain a base. Further, the reaction mixture may be subjected to hydrolysis treatment in advance of separation of the reaction product and the imide compound. The water-insoluble solvent may be a hydrocarbon, an ether, a carboxylic acid, and others. The reaction product may be an oxidation reaction product of an alicyclic hydrocarbon, or an aromatic hydrocarbon having a methyl or methylene group, and is water-insoluble (e.g., a cyclic alcohol, a cyclic ketone, an aldehyde having a cyclic hydrocarbon group or a carboxylic acid having a cyclic hydrocarbon group).

Furthermore, the substrate may be subjected to a reaction in the presence of a co-catalyst.

The present invention also includes a process for separating the imide compound and a metal catalyst from a mixture containing the metal catalyst and the imide compound. In the process, the imide compound and the metal catalyst are separated by (C) a solvent-crystallization step for crystallizing the imide compound by using a solvent for crystallization, (D) an adsorption step for adsorbing the metal catalyst by an adsorption treatment, or (E) an extraction step for distributing the imide compound into a phase of a water-insoluble solvent and the metal catalyst into a phase of an aqueous solvent, respectively by using the aqueous solvent containing at least water and the water-insoluble solvent separable from the aqueous solvent.

In the solvent-crystallization step (C), the solvent for crystallization may be an aqueous solvent (in particular water). The imide compound may be an aromatic imide compound, and the metal catalyst may be soluble in an aqueous solvent.

In the adsorption step (D), the adsorption treatment may be conducted by using an ion-exchanger.

In the extraction step (E), the aqueous solvent may be water, and the water-insoluble solvent may be a hydrocarbon, an alcohol, a nitrile, and/or a mixed solvent thereof. The metal catalyst may be water-soluble.

Furthermore, the present invention also includes a process for regenerating an imide compound represented by the formula (1) from a deactivated imide compound which is formed by employing the imide compound in a reaction. In the regenerating process, the imide compound can be regenerated by hydrolyzing the deactivated imide compound to convert into a dicarboxylic acid or a salt thereof, reacting the dicarboxylic acid or the salt thereof, or a reactive derivative of the dicarboxylic acid with (i) a hydroxylamine or (ii) O-substituted hydroxylamine, and treating with an acid.

Incidentally, in the present specification, the term "crystallization" includes a rinse or repulp treatment comprising washing or crystallizing a desired compound with a relatively small amount of a solvent, and also includes a precipitation.

BEST MODE FOR CARRYING OUT THE INVENTION

Figure 1:
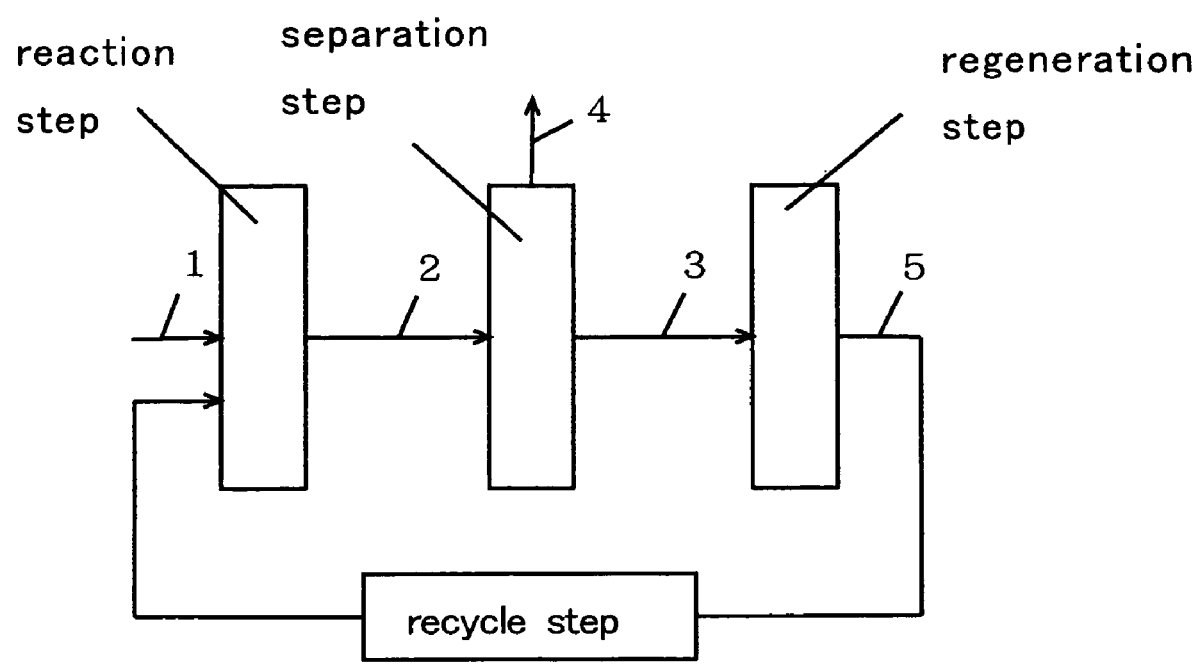
FIG. 1 is a schematic flow-chart for explaining an example of the production process of the present invention.

In the process of the present invention, from a reaction mixture obtained by reacting a substrate in the presence of an imide compound represented by the formula (1) shown below, a reaction product and the imide compound are separated. In the separating process, the imide compound is separated as a crystalline component or non-crystalline component by (A) a crystallization [e.g., (A1) a solvent-crystallization with a solvent for crystallization, (A2) cooling-crystallization] operation, or the imide compound can be separated by extraction operation with an aqueous solvent to shift the imide compound into the aqueous solvent.

[Imide Compound]

An imide compound has an imide unit represented by the following formula (1):

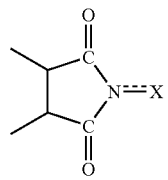

(1)

Wherein X represents an oxygen atom, a hydroxyl group or an acyloxy group.

Examples of the acyloxy group include, for example, an acyloxy group having about 1 to 6 carbon atoms such as formyloxy, acetyloxy(acetoxy), propionyloxy, and butyryloxy groups (preferably a $C_{1-4}$acyloxy group, in particular, acetyloxy group).

Incidentally, in the formula (1), X represents an oxygen atom or a hydroxyl group, and the bond between nitrogen atom N and X is a single bond or a double bond.

A concrete example of the imide compound having the unit shown by the formula (1) (hereinafter, sometimes referred to imide compound of the formula (1)) includes, for example, a compound represented by the following formula (2):

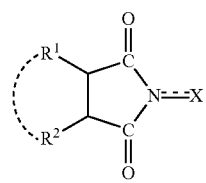

(2)

wherein $R^1$ and $R^2$ are the same or different, each representing a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may bond together to form a double bond or an aromatic- or non-aromatic ring; the aromatic- or non-aromatic ring formed with $R^1$ and $R^2$ may have at least one imide unit represented by the formula (1); and X has the same meaning as defined above.

In the compound of the formula (2), examples of the halogen atom designated by the substitutent $R^1$ or $R^2$ include iodine, bromine, chlorine, and fluorine. Alkyl groups include, e.g., straight- or branched-chain alkyl groups having about 1 to 10 carbon atoms such as methyl, ethyl, propyl, isopropyl, butyl, isobutyl, s-butyl, t-butyl, pentyl, hexyl, heptyl, octyl, and decyl groups (preferably, $C_{1-6}$alkyl groups, particularly $C_{1-4}$alkyl groups).

Aryl groups include phenyl group, naphthyl group and others, and cycloalkyl groups include $C_{3-10}$ cycloalkyl groups such as cyclopentyl, cyclohexyl, and cyclooctyl groups. Alkoxy groups include alkoxy groups having about 1 to 10 carbon atoms, such as methoxy, ethoxy, propoxy and butoxy groups, preferably $C_{1-6}$alkoxy groups, and particularly $C_{1-4}$alkoxy groups.

Alkoxycarbonyl groups include alkoxycarbonyl groups having about 1 to 10 carbons atoms in an alkoxy moiety, such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl, and hexyloxycarbonyl groups (preferably, $C_{1-6}$alkoxy-carbonyl groups, more preferably $C_{1-4}$alkoxy-carbonyl groups).

As the acyl group, there may be exemplified those having about 1 to 6 carbon atoms, such as formyl, acetyl, propionyl, butyryl, isobutyryl, valeryl, isovaleryl, and pivaloyl groups.

The substitutents $R^1$ and $R^2$ may be the same or different. Moreover, in the formula (2), the substitutents $R^1$ and $R^2$ may bond together to form a double bond or an aromatic- or non-aromatic ring. Preferred aromatic- or non-aromatic rings are about 5 to 12-membered ones, particularly about 6 to 10-membered ones. Though the ring may be a heterocycle or a condensed heterocycle, a hydrocarbon ring in many cases. Examples of such ring include non-aromatic alicyclic rings [e.g., cycloalkane rings which may have a substitutent, such as cyclohexane ring; cycloalkene rings which may have a substitutent, such as cyclohexene ring; bridged hydrocarbon rings which may have a substitutent, such as 5-norbornene ring]; and aromatic rings (including a condensed ring) which may have a substitutent, such as benzene ring and naphthalene ring. In many instances, the aforementioned ring is constituted of an aromatic ring.

The ring may have a substitutent such as an alkyl group, a haloalkyl group, a hydroxyl group, an alkoxy group, a carboxyl group, an alkoxycarbonyl group, an acyl group, a nitro group, a cyano group, an amino group and a halogen atom.

Incidentally, the aromatic- or non-aromatic ring composed of the substitutents $R^1$ and $R^2$ may have at least one imide unit represented by the formula (1) (usually, one or two imide units). For example, when $R^1$ or $R^2$ represents an alkyl group having 2 or more carbon atoms, the imide unit shown by the formula (1) may be formed in the adjacent two carbon atoms constituting the alkyl group. Moreover, when $R^1$ and $R^2$ may bond together to form a double bond, the imide unit shown by the formula (1) may be formed in the double bond. Further, when $R^1$ and $R^2$ may bond together to form an aromatic- or non-aromatic ring, the imide unit shown by the formula (1) may be formed in the adjacent two carbon atoms constituting the ring.

The preferred imide compounds include compounds expressed by the following formulae:

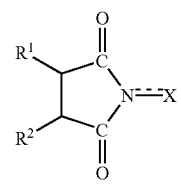

(1a)

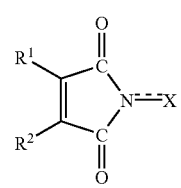

(1b)

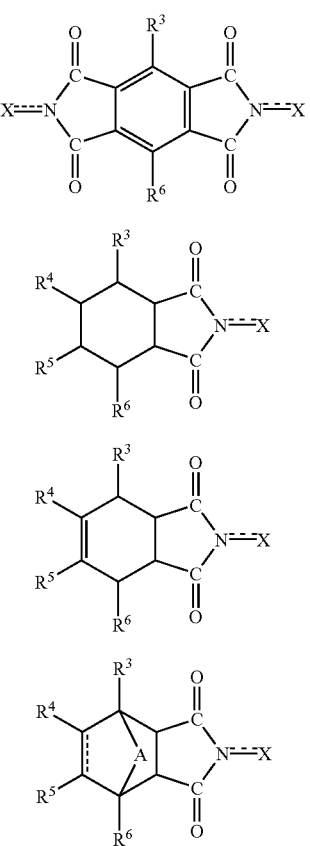

wherein $R^3$ to $R^6$ are the same or different, each representing a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom; each of the adjacent groups of $R^3$ to $R^6$ may be bond together to form an aromatic- or non-aromatic ring; A represents a methylene group or an oxygen atom; and $R^1$, $R^2$, and X have the same meanings as defined above.

As to the substitutents $R^3$ to $R^6$, examples of alkyl groups, alkoxyl groups, alkoxycarbonyl groups, acyl groups, and halogen atoms are similar to those listed above. Examples of haloalkyl groups include $haloC_{1-6}$alkyl groups such as trifluoromethyl group. Usually, the substitutents $R^3$ to $R^6$ each stands for, in many instances, a hydrogen atom, a lower alkyl group having about 1 to 4 carbon atoms, a carboxyl group, a nitro group, or a halogen atom.

The imide compounds are singly or in combination.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-acetoxyphthalimide, N-hydroxyhetimide, N-hydroxyhimimide, N-hydroxytrimellitimide, N,N'-dihydroxypyromellitimide, N,N'-dihydroxynaphthalenetetracarboximide.

The imide compound can be prepared by a conventional imidation reaction, for example, by allowing a corresponding acid anhydride to react with hydroxylamine $NH_2OH$ to ring-open the acid anhydride group, and then closing the ring to form an imide.

The acid anhydrides include, for example, saturated or unsaturated aliphatic dicarboxylic acid anhydrides such as succinic anhydride and maleic anhydride; saturated or unsaturated non-aromatic cyclic polycarboxylic acid anhydrides (alicyclic polycarboxylic acid anhydrides) such as tetrahydrophthalic acid anhydride, hexahydrophthalic acid anhydrides (1,2-cyclohexane dicarboxylic acid anhydride), 1,2-anhydride of 1,2,3,4-cyclohexanetetracarboxylic acid; bridged cyclic polycarboxylic acid anhydrides (alicyclic polycarboxylic acid anhydrides) such as hetic acid anhydride and himic acid anhydride; and aromatic polycarboxylic acid anhydrides such as phthalic anhydride, tetrabromophthalic anhydride, tetrachlorophthalic anhydride, nitrophthalic anhydride, trimellitic anhydride, methylcyclohexene tricarboxylic acid anhydride, pyrromellitic anhydride, mellitic anhydride, and 1,8;4,5-naphthalenetetracarboxylic acid dianhydrides.

A particularly preferred compound includes a cyclic imide compound [an N-hydroxyimide compound derived from an alicyclic polycarboxylic anhydride, especially one derived from an aromatic polycarboxylic anhydride, for example, an aromatic imide compound (a hydrophobic imide compound or a water-insoluble imide compound) such as N-hydroxyphthalimide and N-acetoxyphthalimide].

Incidentally, such imide compounds can be utilized as a catalyst for a variety of reactions (e.g., oxidation reaction, carboxylation reaction, nitration reaction, sulfonation reaction, acylation reaction, radical-coupling reaction). In particular, just contacting a substrate with oxygen in the presence of the imide compound can provide an alcohol, a ketone, a carboxylic acid, and a lactone with high selectivity and yield.

The amount of the imide compound of the formula (1) can be selected within a wide range, and may for example be about $1 \times 10^{-6}$ mol ($1 \times 10^{-4}$ mol %) to 1 mol (100 mol %), preferably about $1 \times 10^{-5}$ mol ($1 \times 10^{-3}$ mol %) to 0.5 mol (50 mol %), and more preferably about $1 \times 10^{-4}$ mol ($1 \times 10^{-2}$ mol %) to 0.4 mol (40 mol %) relative to 1 mol of a substrate, with about $1 \times 10^{-4}$ mol ($1 \times 10^{-2}$ mol %) to 0.35 mol (35 mol %) of the imide compound practically employed.

Incidentally, use of the imide compounds in a reaction sometimes results in deactivation or modification of part or all of the imide compounds depending upon the species of the reaction and a reaction condition. The typical examples of such deactivated or decomposed product (deactivated catalyst) include a N-substituted or non-substituted cyclic imide compound having a unit represented by the following formula (4), a cyclic acid anhydride having a unit represented by the following formula (5), and a ring-opened derivative thereof:

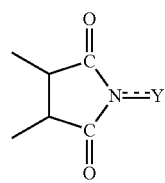

(4)

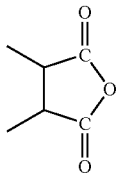

(5)

wherein Y represents a hydrogen atom or an alkoxy group.

Examples of the alkoxy group include, for example, an oxy group substituted with the group corresponding to a substrate (e.g., hydrocarbons such as a cycloalkane), such as a hydrocarbon group-substituted oxy group (e.g., a $C_{3\text{-}20}$cycloalkyloxy group). For example, when a cyclohexane as a substrate is oxidized, a compound can be produced which has a unit represented by the formula (4) wherein the group Y is cyclohexyloxy group.

Moreover, for example, when N-hydroxyphthalimide is used as the imide compound, there can be produced a phthalimide formed by reduction during a reaction (a compound of the formula (4) wherein the group Y is hydrogen atom), N-substituted oxyphthalimide corresponding to a substrate (a compound of the formula (4) wherein the group Y is an alkoxy group), phthalic anhydride formed by hydrolysis during a reaction followed by dehydrating to ring-close (a compound of the formula (5)) and a ring-open derivative thereof (a dicarboxylic acid such as phthalic acid).

These deactivated catalysts can be regenerated in the aftermentioned step for regenerating the imide compound.

[Co-Catalyst]

The imide compound may be used in combination with a co-catalyst. As the co-catalyst (sometimes referred to as a metal catalyst or metal co-catalyst), there may be mentioned a metal compound, for example, such as transition metal-containing compounds and compounds containing a Group 13 element of the Periodic Table of Elements (e.g., boron B, Aluminum Al) typified by a boron compound. The co-catalyst can be used either singly or in combination.

As the transition metal element, there may be mentioned, for instance, Group 3 elements of the Periodic Table of Elements (e.g., besides scandium Sc and yttrium Y, lanthanoid elements such as lanthanum La, cerium Ce, samarium Sm; actinoid elements such as actinium Ac), Group 4 elements of the Periodic Table of Elements (e.g., titanium Ti, zirconium Zr, hafnium Hf), Group 5 elements (e.g., vanadium V, niobium Nb, tantalum Ta), Group 6 elements (e.g., chromium Cr, molybdenum Mo, tungsten W), Group 7 elements (e.g., manganese Mn), Group 8 elements (e.g., iron Fe, ruthenium Ru, osmium Os), Group 9 elements (e.g., cobalt Co, rhodium Rh, iridium Ir), Group 10 elements (e.g., nickel Ni, palladium Pd, platinum Pt), and Group 11 elements (e.g., copper Cu, silver Ag, gold Au) of the Periodic Table of Elements.

Particularly, when combined with an imide compound of the formula (1), a compound containing a lanthanoid element such as Ce, a Group 4 element such as Ti, a Group 5 element such as V and Nb, a Group 6 element such as Cr, Mo and W, a group 7 element such as Mn, a Group 8 element such as Fe and Ru, a Group 9 element such as Co and Rh, a Group 10 element such as Ni, a Group 11 element such as Cu, or a Group 13 element such as B and Al exhibits high oxidation activity.

There is no specific restriction on the species of the co-catalyst (co-oxidizing agent or promoter) provided that it contains an element selected from the elements listed above and has the catalytic ability. The co-oxidizing agent may be a hydroxide but is usually a metal oxide, a hydride, a nitride, an oxygen acid or a salt thereof, an oxygen acid ester, an organic acid salt, an inorganic acid salt, a halide, a coordination compound (complex), a heteropolyacid or a salt thereof, which contains an element of those listed above. Further, as the boron compound, there may be exemplified boron hydrides (e.g., borane, diborane, tetraborane, pentaborane, decaborane), boric acids (e.g., orthoboric acid, methaboric acid, tetraboric acid), borates (salts of boric acid) (e.g., nickel borate, magnesium borate, manganese borate), boron oxides such as $B_2O_3$, borazane, borazene, borazine, boron amide, boron imide, and other nitrogen-containing compounds, $BF_3$, $BCl_3$, tetrafluoroborate and other halides, and esters of boric acid (e.g., methyl borate, phenyl borate).

As the organic acid salt, there may be mentioned, for example, $C_{1\text{-}30}$-carboxylates (e.g., $C_{2\text{-}24}$-carboxylates) such as acetates, propionates, salts of naphthenic acid, octylate, and stearates, and examples of the inorganic acid salt are nitrates, sulfates, and phosphates. Moreover, as the halide, there may be exemplified chlorides and bromides.

As a ligand of the complex, there may be exemplified OH (hydroxo); alkoxy groups such as methoxy, ethoxy, propoxy and butoxy groups; acyl groups such as acetyl and propionyl groups; alkoxycarbonyl groups such as methoxycarbonyl (acetato) and ethoxycarbonyl groups; acetylacetonato, cyclopentadienyl group; halogen atoms such as chlorine and bromine; CO; CN; oxygen atom; $H_2O$ (aquo); phosphorus compounds such as phosphine (e.g., a triarylphosphine such as triphenylphosphine); and nitrogen-containing compounds such as $NH_3$ (ammine), NO, $NO_2$ (nitro), $NO_3$ (nitrato), ethylenediamine, diethylenetriamine, pyridine and phenanthroline. As to the complex or a complex salt, a single ligand or ligands of the same or different kinds may be coordinated therein.

Preferred complexes include complexes containing a transition metal element selected from those mentioned above. The complex may be constituted of a combination of a transition metal element and a ligand that are suitably selected from the above. For example, the complex may be ceriumacetylacetonato, vanadiumacetylacetonato, cobaltacetylacetonato, rutheniumacetylacetonato, or copperacetylacetonato.

A polyacid which forms the heteropolyacid contains, for example, in many cases, at least one of the Group 5 elements or the Group 6 elements of the Periodic Table of Elements, such as V (vanadic acid), Mo (molybdic acid), and W (tungstic acid). There is no specific restriction as to the central atom. Concrete examples of the heteropoly acid include cobaltmolybdate, cobalttungstate, molybdenumtungstate, vanadiummolybdate, and vanadomolybdenumphosphate.

When a co-catalyst containing the Group 7 element and/or the Group 9 element [e.g., the combination of the Group 7 element-containing compound and the Group 9 element-containing compound (in particular, the combination of manganese-containing compound and cobalt-containing compound)] is employed as the co-catalyst, an aliphatic dicarboxylic acid (in particular, adipic acid) or an aromatic carboxylic acid (e.g., terephthalic acid) is efficiently produced.

It is preferred that the metal catalyst is soluble in the solvent crystallizable of a reaction product or an imide compound (in particular, an aqueous solvent such as water and water-containing solvent). The preferred metal catalyst includes, for example, an organic acid salt (e.g., acetate), an inorganic acid salt (e.g., sulfate), a halide (e.g., chloride), an oxide, a complex, a heteropolyacid, in particular, an organic acid salt, a complex.

The imide compound, or a catalytic system comprised of the imide compound (I) and the above-described co-catalyst may be either homogeneous or heterogeneous. Further, the catalytic system may be a solid catalyst comprising a catalytic component supported on a support or carrier. As the support, in many instances, a porous support such as active carbon, zeolite, silica, silica-alumina, and bentonite is used. As to the amount of the catalytic component supported on the support in the solid catalyst, the amount of the imide compound of the formula (1) is about 0.1 to 50 parts by weight relative to 100 parts by weight of the support. The amount of the co-catalyst supported is, relative to 100 parts by weight of the support, about 0.1 to 30 parts by weight.

The amount of the co-catalyst is, for example, about $1 \times 10^{-6}$ mol to 0.7 mol, preferably about $1 \times 10^{-5}$ mol to 0.3 mol, more preferably about $1 \times 10^{-5}$ mol to 0.1 mol (10 mol %), and may be about $1 \times 10^{-6}$ mol to $1 \times 10^{-2}$ mol, and particularly about $1 \times 10^{-6}$ mol to $1 \times 10^{-3}$ mol, relative to 1 mol of a substrate. When the heteropolyacid or a salt thereof is used as the co-catalyst, the amount thereof is, relative to 100 parts by weight of a substrate, about 0.1 to 25 parts by weight, preferably about 0.5 to 10 parts by weight, and more preferably about 1 to 5 parts by weight.

The concentration of the co-catalyst in liquid-phase reaction system may be usually about 1 to 10,000 ppm, preferably about 5 to 5,000 ppm, and more preferably about 10 to 3,000 ppm on weight basis.

Incidentally, the ratio of the co-catalyst relative to the imide compound is, for example, imide compound/co-catalyst=95/5 to 5/95 (molar ratio), preferably about 90/10 to 20/80 (molar ratio), and more preferably about 85/15 to 50/50 (molar ratio).

[Substrate]

The species of a substrate is not particularly limited to a specific one, and includes various substrates disclosed in Japanese Patent Application Laid-Open No. 327626/1997 (JP-A-9-327626) such as a hydrocarbon, an alcohol, an aldehyde, a ketone, an amine, a heterocyclic compound, a thiol, a sulfide, and an amide. The preferred substrate includes a hydrocarbon, an alcohol, an aldehyde, a ketone, and others.

As the hydrocarbon, for example, there may be mentioned a saturated or unsaturated aliphatic hydrocarbon which may have a substitutent, a saturated or unsaturated alicyclic hydrocarbon which may have a substitutent [e.g., a cycloalkane, a cyclic olefin, a polycycloalkane, a bridged cyclic hydrocarbon having a tertiary carbon atom (methine carbon), a hydrogenation product of a condensed cyclic hydrocarbon], a condensed cyclic hydrocarbon containing a non-aromatic ring such as a partial-hydrogenation condensed polycyclic hydrocarbon, an aromatic hydrocarbon in which a methyl group or a methylene group is bound to an aromatic ring.

As the saturated or unsaturated aliphatic hydrocarbon, for example, there may be mentioned $C_{4-20}$ saturated hydrocarbons such as butane, isobutane, pentane, hexane, octane and decane; $C_{4-20}$ olefinic hydrocarbons such as 2-butene and isobutene; linear and branched aliphatic hydrocarbons such as conjugate dienes (e.g., butadiene (1,3-butadiene), isoprene (2-methyl-1,3-butadiene)). The preferred aliphatic hydrocarbons include branched saturated hydrocarbons such as isobutane, branched unsaturated hydrocarbons such as isobutene and conjugate dienes such as butadiene, and isoprene.

Among the saturated or unsaturated alicyclic hydrocarbons, preferred alicyclic hydrocarbons include alicyclic hydrocarbons having about 3 to 30 members, preferably about 3 to 25 members, and in particular about 3 to 20 members (for example, about 5 to 20 members, especially about 5 to 16 members).

The cycloalkanes include, for instance, $C_{3-30}$ cycloalkanes such as cyclobutane, cyclopentane, cyclohexane, cycloheptane, cyclooctane, cyclononane, cyclodecane, cycloundecane, cyclododecane, cyclotridecane, cyclotetradecane, cyclooctadecane, cycloeicosane, cyclodocosane, cyclotetracosane, or cyclotriacontane (preferably $C_{4-20}$ cycloalkanes, more preferably $C_{4-16}$ cycloalkanes).

The cyclic olefins include, for example, $C_{3-30}$ cycloalkenes (preferably $C_{4-20}$ cycloalkenes, more preferably $C_{4-16}$ cycloalkenes) such as cyclopropene, cyclobutene, cyclopentene, cyclohexene, cycloheptene, cyclooctene, cyclononene, and cyclodecene; cycloalkadienes (e.g., $C_{3-30}$ cycloalkadienes, preferably $C_{4-20}$ cycloalkadienes, more preferably $C_{4-16}$ cycloalkadienes such as cyclopentadiene, 1,3-cyclohexadiene, 1,4-cyclohexadiene, 1,3-cycloheptadiene and other cycloheptadienes, 1,5-cyclooctadiene and other cyclooctadienes); cycloalkatrienes (e.g., $C_{4-16}$ cycloalkatrienes such as cyclooctatriene); cycloalkatetraenes (e.g., $C_{4-16}$ cycloalkatetraenes such as cyclooctatetraene), and so forth.

As bridged cyclic hydrocarbons, there may be mentioned, for example, bicyclic hydrocarbons (e.g., pinane, pinene, bornane, norbornane, norbornene, bicyclo[3.2.1]octane, bicyclo[4.3.2]undecane), tricyclic hydrocarbons (e.g., adamantane, exotricyclo[5.2.1.0$^{2,6}$]decane, endotricyclo [5.2.1.0$^{2,6}$]decane), tetracyclic hydrocarbons (e.g., tetracyclo[4.4.0.1$^{2,5}$.1$^{7,10}$]dodecane), and dicyclohexadiene, dicyclopentadiene and other dimers of dienes, hydrogenated products of these dimers (e.g., dicyclohexane, dicyclopentane), their derivatives and terpenes (e.g., monocyclic monoterpenes, bicyclic monoterpenes, monocyclic sesquiterpenes, bicyclic sesquiterpenes, tricyclic sesquiterpenes, diterpenes, triterpenes, tetraterpenes, polyterpenes and derivatives thereof), and others.

As a bridged cyclic hydrocarbon, bi-, tri- or tetracyclic hydrocarbon having about 7 to 16 constitutive carbon atoms of the rings (in particular, about 6 to 14 constitutive carbon atoms of the rings) such as pinane, bornane, norbornane, norbornene, adamantane may be employed in many cases.

The condensed polycyclic hydrocarbon containing a non-aromatic ring such as complete or partial hydrogenated condensed polycyclic hydrocarbon includes, for example, acenaphthene, fluorene, tetralin, indene, indan, perhydroanthracene, perhydrophenanthrene, perhydrophenalene, perhydroacenaphthene, decalin, hexahydroindane and so on. In the condensed polycyclic hydrocarbon, a 5- to 8-membered ring (in particular, 5- or 6-membered ring) may practically be condensed.

The polycyclic hydrocarbons such as the condensed polycyclic hydrocarbons and bridged cyclic hydrocarbons include compounds having at least one methylidyne group (i.e., methine carbon-hydrogen bond —CH<) in the bridgehead positions and/or junction positions (fusing sites between rings).

The aromatic hydrocarbon in which methyl group or methylene group is bound to the aromatic ring may be a compound having at least one methyl group or methylene group being substituted on the aromatic ring. The aromatic ring may be whichever of an aromatic hydrocarbon ring or an aromatic heterocyclic ring. As examples of such compounds, there may be mentioned toluene, (o-, m-, p-)xylene, 1,2,3-trimethylbenzene, mesitylene, 1,2,3,4-tetramethylbenzene, durene, 4-t-butyl-1-methylbenzene, ethylbenzene, propylbenzene, cumene, o-, m- or p-ethyltoluene, 1-methylnaphthalene, 2-methylnaphthalene, 1,5-dimethylnaphthalene, 2,5-dimethylnaphthalene, 1-methylanthracene, 2-methylanthracene, 9-methylanthracene, 4,4'-dimethylbiphenyl, dibenzyl, diphenylmethane, and triphenylmethane. Among them, a $C_{6-10}$ aromatic hydrocarbon having about 1 to 4 methyl groups in its molecule is particularly preferred.

The preferred hydrocarbons include (1) conjugate dienes (e.g., butadiene, isoprene), (2) compounds having a carbon-hydrogen bond at a moiety adjacent to unsaturated bond (e.g., $C_{4-20}$olfeins such as 2-butene), (3a) 5- to 16-membered cycloalkanes such as cyclohexane and methylclohexane, (3b) 5- to 16-membered cycloalkene such as cyclohexene, (4) condensed cyclic compound containing a non-aromatic ring (e.g., a cycloalkane ring or a heterocyclic ring) such as decalin, tetralin and fluorene, (5) bridged cyclic hydrocarbons having a tertiary carbon atom (methine carbon) such as adamantane and norbornene, (6) aromatic hydrocarbons in which methyl group or methylene group is bound to its aromatic ring (e.g., $C_{6-10}$ aromatic hydrocarbons having 1 to 4 methyl groups such as toluene, (o-, m-, p-)xylene, p-t-butyltoluene; aromatic hydrocarbons in which methylene group is bound to its aromatic ring such as diphenylmethane).

Examples of the alcohols as a substrate include alcohol derivatives corresponding to the hydrocarbons, and include, for example, aliphatic primary or polyalcohols, alicyclic primary or polyalcohols, or aromatic primary or polyalcohols.

As the aliphatic primary alcohol, there may be mentioned, for example, $C_{1-20}$ saturated aliphatic alcohols (preferably $C_{1-12}$ saturated aliphatic alcohols, more preferably $C_{1-8}$ saturated aliphatic alcohols) such as methanol, ethanol, 1-propanol, isopropanol, 1-butanol, isobutanol, 1-pentanol, 2-pentanol, neopentyl alcohol, 1-hexanol, 1-octanol, 1-decanol, 1-dodecanol, myristyl alcohol and 1-hexadecanol; $C_{2-20}$ unsaturated aliphatic alcohols (preferably $C_{3-10}$ unsaturated aliphatic alcohols) such as allyl alcohol, crotyl alcohol, propargyl alcohol, citronellol and geraniol.

As the aliphatic polyalcohol, there may be mentioned, for example, ethylene glycol, propylene glycol, trimethylene glycol, 1,2-butanediol, 1,3-butanediol, 1,4-butanediol, 1,6-hexanediol, 2,5-hexanediol, neopentyl glycol, pinacol and glycerin.

As the alicyclic primary alcohol, there may be mentioned, for example, alicyclic primary alcohol having 5 to 30 members such as cyclopentanol, cyclohexanol, cycloheptanol, cyclooctanol, cyclodecanol, cycloundecanol, cyclododecanol, cyclotetradecanol, cycloeicosanol, methylcyclohexanol, cyclohexen-1-ol, cycloocten-1-ol, cyclogeraniol, borneol, menthol, adamantanol, camphenilol and borneol. The preferred alicyclic alcohols include compounds having 5 to 30 members, preferably 5 to 25 members, in particular 5 to 20 members (e.g., 5 to 16 members) such as cycloalkanol and polycycloalkanol.

The alicyclic polyalcohols include, for example, 1,2-cyclohexanediol, 1,4-cyclohexanediol, adamantanediol and adamantanetriol.

The aromatic alcohols include, for example, $C_{6-20}$aryl alcohol (preferably $C_{7-12}$aryl alcohol) such as benzyl alcohol, salicyl alcohol, benzhydrol, and phenethyl alcohol.

Among these alcohols, primary alcohols and secondary alcohols are preferred, and they are whichever of aliphatic alcohols, alicyclic alcohols or aromatic alcohols.

The preferred alcohols include (a) compounds having a hydroxyl group at a moiety adjacent to unsaturated bond (e.g., unsaturated aliphatic alcohols and aromatic alcohols such as allyl alcohols, benzyl alcohols, benzhydrol), (b) alicyclic alcohol (e.g., $C_{5-16}$cycloalkanol such as cyclohexanol and methylcyclohexanol), (c) alicyclic alcohols having a tertiary carbon atom (methine carbon) such as borneol.

Examples of aldehydes as a substrate include aldehyde derivatives corresponding to the hydrocarbons, and include, for example, aliphatic aldehyde [$C_{1-20}$saturated aliphatic aldehydes (preferably $C_{1-10}$saturated aliphatic aldehydes) such as formaldehyde, acetoaldehyde, propionaldehyde, butylaldehyde, hexanal, octanal and nonanal; unsaturated aliphatic aldehydes such as acrolein, geranial and citronellal; aliphatic polyaldehyde such as glyoxal, malonaldehyde, succinaldehyde, glutaraldehyde, adipic aldehyde, pimelic aldehyde, suberic aldehyde and sebacic aldehyde]; aromatic aldehydes such as benzaldehyde, oxybenzaldehyde, cinnamalaldehyde, salicylaldehyde, anisaldehyde, 1-naphthylaldehyde, vanillin (vanillaldehyde), phthalaldehyde, isophthalaldehyde and terephthalaldehyde; alicyclic aldehydes such as formylcyclohexane; heterocyclic aldehydes such as nicotinaldehyde and furfural.

Examples of ketones as a substrate include ketone derivatives corresponding to the hydrocarbons, and include, for example, aliphaticketones, alicyclic ketones, aromatic ketones and heterocyclic ketones.

The aliphatic ketones include, for example, $C_{2-20}$aliphatic ketones (preferably $C_{2-12}$aliphatic ketones) such as acetone, methyl ethyl ketone, diethyl ketone, dipropyl ketone, methyl propyl ketone, methyl butyl ketone, and pinacolone.

The alicyclic ketones include, for example, 4- to 30-membered alicyclic ketones (cyclic ketones) such as cyclobutanone, cyclopentanone, cyclohexanone, cyclooctanone, cyclononanone, cyclodecanone, cycloundecanone, cyclododecanone, cyclotetradecanone, cyclooctadecanone, cycloeicosanone, 2-methylcyclohexanone, 2-ethylcyclohexanone, 2,6-dimethylcyclohexanone, 4-chlorocyclohexanone, 4-methoxycyclohexanone, cyclohexanedione, cyclopentenone, cyclohexenone, cyclooctenone, cyclodecenone, menthone, and camphor. The preferred alicyclic ketones include 5- to 20-membered, in particular, 5- to 16-membered compounds.

The aromatic ketones include, for example, acetophenone, propiophenone, benzophenone, deoxybenzoin, and 1-naphthalenone. The heterocyclic ketones include, for example, heterocyclic ketones such as inden-1-one, 1,2,3-indantrione, fluoren-9-one, and 4-pyranone.

It is preferred that amines as a substrate are primary or secondary amines such as aliphatic amines such as methylamine, ethylamine, propylamine, butylamine, dimethylamine, diethylamine, dibutylamine, ethylenediamine, 1,4-butanediamine, hydroxylamine and ethanolamine; alicyclic amines such as cyclopentylamine and cyclohexylamine; aromatic amines such as benzylamine and toluidine.

Examples of the heterocyclic compounds as a substrate include (a) non-aromatic heterocyclic compounds or condensed cyclic hydrocarbons having a non-aromatic heterocyclic ring (e.g., pyran, pyrazoline, piperazine, indoline, isoindoline, chromene, xanthene, chroman, isochroman), and non-aromatic heterocyclic compounds or condensed cyclic hydrocarbons having a non-aromatic heterocyclic ring substituted by an alkyl group (e.g., alkyl groups having about 1 to 6 carbon atoms such as methyl, ethyl group), (b)

heterocyclic compounds having an aromatic heterocyclic ring and a methyl group or a methylene group at a position adjacent to the aromatic heterocyclic ring (e.g., heterocyclic compounds which has an aromatic heterocyclic containing 1 to 3 heteroatoms selected from an oxygen atom, a sulfur atom and a nitrogen atom and substituted by an alkyl group having about 1 to 6 carbon atoms, such as 2-methylfuran, 2,5-dimethylfuran, 2-methylthiophene, 2,5-dimethylthiophene, 2-methylpyridine, 3-methylpyridine, 4-methylpyridine, 2,5-dimethylpyridine, 3-ethylpyridine, and 2-methylquinoline).

Examples of the thiols as a substrate include, for example, ethanethiol and phenylmethanethiol. Examples of the sulfide include, for example, diethyl sulfide, methyl propyl sulfide and diphenyl sulfide. Moreover, examples of the amides include, for example, formamide and acetoamide.

Incidentally, a substrate substituted by various substitutents (e.g., a halogen atom, an alkyl group, an alkenyl group, an aryl group, a heterocyclic group, an oxo group, a hydroxyl group, an alkoxy group, a hydroxyalkyl group, a carboxyl group, an alkoxycarbonyl group, an acyl group, an amino group, a substituted amino group, a cyano group, a nitro group) may be used as a substrate.

As the substrate having such a substituent, for example, there may be mentioned a substrate having an alkyl group containing 2 or more carbon atoms (e.g., $C_{2-10}$alkyl groups such as ethyl, propyl, butyl, t-butyl, hexyl and octyl groups), a substrate having a halogen atom (e.g., fluorine, chlorine, and bromine atoms), a substrate having a carbonyl group (e.g., ketones such as cyclohexanone and adamantanone), a substrate having a hydroxyl group (e.g., alcohols such as cyclohexanol and adamantanol), a substrate having a carboxyl group (e.g., carboxylic acids such as carboxytoluene) or a derivative thereof (e.g., esters), a mixture thereof (KA oil) and an ester thereof (e.g., cyclohexyl acetate and acetyloxytoluene).

In the separating process comprising the solvent-crystallization step (A1), the species of the substrate is not particularly limited to a specific one, but it is preferred that a substrate which forms a soluble compound in the specific solvent (hydrocarbons, chain ethers or water). As such a substrate, there may be mentioned, for example, an alicyclic hydrocarbon [e.g., a cycloalkane, polycycloalkane], and an alicyclic or aromatic alcohol [e.g., an alcohol corresponding to the cycloalkane or the aromatic hydrocarbon].

As the cycloalkane, there may be mentioned, the above-exemplified cycloalkane [e.g., $C_{4-20}$cycloalkanes (preferably $C_{4-16}$cycloalkanes, more preferably $C_{4-12}$cycloalkanes), such as cyclobutane, cyclopentane, cyclohexane, cycloheptane, cyclooctane, methylcyclohexane, ethylcyclohexane, dimethylcyclohexane, chlorocyclohexane, methoxycyclohexane, cyclooctane, cyclononane, cyclododecane, cyclopentadecane, and cyclooctadecane]. The cycloalkanol includes an alcohol corresponding to the cycloalkane [e.g., a $C_{4-16}$alcohol such as hexanol].

The preferred cycloalkane includes a $C_{4-10}$cycloalkane (preferably a $C_{5-8}$cycloalkane) such as cyclohexane, methylcyclohexane and cyclooctane.

The polycycloalkane includes the above bridged cyclic hydrocarbon and the above complete hydrogenated condensed polycyclic hydrocarbon, and includes, for example, a compound having a tertiary carbon atom at bridgehead position (e.g., a bicyclic hydrocarbon such as bornane, norbornane and norbornene, a tricyclic hydrocarbon such as tricyclo[4.3.1.1$^{2,5}$]undecane, homobrendane and adamantane, a tetracyclic hydrocarbon, terpene), hydrogenated product of condensed polycyclic aromatic hydrocarbon (e.g., decalin, perhydroanthracene, perhydrophenanthrene).

The polycycloalkanol includes an alcohol corresponding to the above cycloalkanol [e.g., an alcohol having a hydroxyl group at a bridgehead position such as adamantanol, adamantanediol, adamantanetriol].

In the separating process comprising the cooling crystallization step (A2), the species of the substrate is not particularly limited to a specific one, and the substrate may be whichever a substrate which forms a water-soluble compound at a crystallization temperature or a substrate which forms a water-insoluble compound at a crystallization temperature. The preferred substrate forms a water-insoluble compound (e.g., a compound which is in the form of solid at an ordinary temperature (about 15 to 25° C.)). As such substrates, there may be mentioned, for example, a substrate which forms water-insoluble carboxylic acid [in particular, a cycloalkane or a polycycloalkane which can form an aliphatic carboxylic acid having 6 or more (preferably 6 to 16, more preferably 6 to 12) carbon atoms, or a methyl group-containing aromatic compound which can form an aromatic carboxylic acid (e.g., an aromatic polycarboxylic acid such as an aromatic dicarboxylic acid)].

As the cycloalkane, there may be mentioned the aforementioned cycloalkane (e.g., a $C_{6-16}$cycloalkane, preferably a $C_{6-12}$cycloalkane), and the aforementioned polycycloalkane (e.g., a compound having a tertiary carbon atom at a bridgehead, a hydrogenation product of a condensed polycyclic aromatic hydrocarbon).

The aromatic compound containing a methyl group includes, for instance, a compound having an aromatic ring substituted by at least one (e.g., about 1 to 10, preferably about 1 to 8) methyl group(s). The aromatic ring may be whichever an aromatic hydrocarbon ring or an aromatic heterocyclic ring. An aromatic hydrocarbon containing a methyl group includes various compounds each having an aromatic hydrocarbon ring (including di- or triaryl-$C_{1-3}$alkane such as diphenylmethane, triphenylmethane, dibenzyl and stilbene) substituted by a methyl group, and includes, for example, an aromatic hydrocarbon substituted with about 1 to 6 methyl groups such as toluene, (o-, m-, p-)xylene, trimethylbenzene (e.g., 1,2,3-trimethylbenzene, 1,3,5-trimethylbenzene), tetramethylbenzene (e.g., 1,2,3,4-tetramethylbenzene, 1,2,4,5-tetramethylbenzene), hexamethylbenzene, 4-t-butyl-1-methylbenzene, 2-methoxy-1-methylbenzene, 1-methylnaphthalene, 2-methylnaphthalene, 1,5-dimethylnaphthalene, 2,5-dimethylnaphthalene. The preferred aromatic hydrocarbon containing a methyl group includes a $C_{6-10}$aromatic hydrocarbon substituted with about 1 to 4 (in particular about 1 to 2) methyl groups in a molecule (e.g., toluene, xylene, tetramethylbenzene).

As a heterocyclic compound containing a methyl group, there may be mentioned a compound having a heterocyclic ring substituted by a methyl group, for example, 2-methylfuran, 3-methylfuran, 2-methylpyran, 3-methylpyran, 3,4-dimethylpyran, methylchromane, picolines (2-, 3- or 4-methylpyridine), lutidines (2,3-dimethylpyridine, 2,4-dimethylpyridine, 2,5-dimethylpyridine, 3,5-dimethylpyridine), collidines (e.g., 2,3,4-trimethylpyridine, 2,3,5-trimethylpyridine, 2,4,6-trimethylpyridine), methylindoles (e.g., 4-methylindole, 5-methylindole, 7-methylindole).

In the extraction process (B), the species of the substrate is not particularly limited to a specific one, but it is preferred that a substrate which forms a compound having an affinity or elution-ability for a water-insoluble solvent. Such reaction products include, for example, an alcohol (e.g., an aliphatic alcohol (in particular, a primary alcohol), an alicyclic monol, an alicyclic diol), an aldehyde, a ketone, a carboxylic acid (e.g., an aliphatic monocarboxylic acid, an alicyclic monocarboxylic acid, an aromatic monocarboxylic acid, an aromatic dicarboxylic acid and other aromatic carboxylic acids, a heterocyclic carboxylic acid), an epoxy compound, an ester, an acid anhydride, a lactone, an acetal, an ether, a sulfide, an amide, a lactam, a Schiff base, an oxime, a nitro compound, an organic sulfur-containing acid, a hydrocarbon, each having about 5 to 30, preferably about 6 to 30 carbon atoms. The particularly preferred reaction product includes a cyclic alcohol [e.g., the aforementioned alicyclic alcohol (a $C_{6-12}$cycloalkanol such as cyclohexanol), an aromatic alcohol (e.g., a $C_{7-12}$aralkyl alcohol such as benzyl alcohol)], a cyclic ketone [e.g., the aforementioned alicyclic ketone (a $C_{6-12}$cycloalkanone such as cyclohexanone), the aforementioned aromatic ketone (a $C_{6-12}$aromatic ketone such as acetophenone, benzophenone, fluorenone)], an aldehyde having a cyclic hydrocarbon group [the aforementioned alicyclic aldehyde (e.g., a $C_{6-12}$aliphatic aldehyde such as hexanal), the aforementioned aromatic aldehyde (e.g., a $C_{7-12}$aromtic aldehyde such as benzaldehyde)], an carboxylic acid having a cyclic hydrocarbon group [e.g., an aromatic carboxylic acid (a $C_{7-12}$aromatic carboxylic acid such as benzoic acid)].

As a substrate which forms such reaction products, there may be mentioned a hydrocarbon which can form a water-insoluble compound [in particular, an alicyclic hydrocarbon (a mono- or polycycloalkane), an aromatic hydrocarbon containing a methyl group or a methylene group].

As such substrates, there may be mentioned the above cycloalkane (e.g., a $C_{4-10}$cycloalkane, preferably a $C_{5-8}$cycloalkane), or the above polycycloalkane (e.g., a compound having a tertiary carbon atom at a bridgehead position, a hydrogenation product of a condensed polycyclic aromatic hydrocarbon).

The aromatic hydrocarbon containing a methyl group or a methylene group includes, for example, the above aromatic hydrocarbon [e.g., a $C_{6-10}$aromatic hydrocarbon substituted by about 1 to 4 methyl groups in a molecule such as toluene and xylene, an aromatic hydrocarbon containing a methylene group such as dibenzyl, diphenylmethane, triphenylmethane], a condensed polycyclic hydrocarbon containing a methylene group such as fluorene.

[Reactions Utilizing the Imide Compound]

The imide compound has the catalytic ability for a variety of reactions (oxidation reaction, carboxylation reaction, nitration reaction, sulfonation reaction, acylation reaction, radial-coupling reaction).

(Oxidation Reaction)

The oxidation reaction of the hydrocarbon can be carried out in the presence of the imide compound to form an oxidation product such as an alcohol, an aldehyde, a ketone, a carboxylic acid, an epoxy compound, a lactone, an acid anhydride, an acetal and an ester corresponding to the substrate. For example, a conjugated iene is oxidized to form the corresponding alkenediol. For instance, an oxide obtained by oxidizing butadiene is a butenediol (cis- or trans-form of 2-buten-1,4-diol, or 1-buten-3,4-diol), and a position of a hydroxyl group is not particularly limited to a specific one. A compound having a carbon-hydrogen bond at a moiety adjacent to an unsaturated bond is oxidized at the moiety adjacent to the unsaturated bond.

Moreover, when an alicyclic hydrocarbon is oxidized, a hydroxyl group or an oxo group is introduced into the ring, or the ring is oxidatively cleaved depending on a condition to form a dicarboxylic acid. When a condensed cyclic compound containing a non-aromatic ring is oxidized, a hydroxyl group or an oxo group is introduced into the non-aromatic ring, or the ring is cleaved depending on a condition to a dicarboxylic acid. When a bridged cyclic hydrocarbon having a tertiary carbon atom (methine carbon atom) is oxidized, a hydroxyl group is introduced into the tertiary carbon atom (e.g., bridgehead site), or an oxo group is introduced into the adjacent site thereto depending on conditions. When an aromatic hydrocarbon in which a methyl group or a methylene group is bound to the aromatic ring is oxidized, the methyl group or the methylene group is oxidized to form the corresponding alcohol, aldehyde, ketone or carboxylic acid depending on conditions.

An alcohol is oxidized with oxygen in the presence of the imide compound to form the corresponding aldehyde, ketone or carboxylic acid. For example, an alicyclic alcohol is oxidized to form the corresponding alicyclic ketone or polycarboxylic acid depending on the oxidation degree. Concretely, 2-methylcyclohexanol is oxidized to form 2-methylcyclohexanone, and further 2-methyladipic acid.

An aldehyde is oxidized with oxygen in the presence of the imide compound to form the corresponding carboxylic acid. For example, adipic aldehyde is oxidized to form adipic acid.

A ketone is oxidized with oxygen in the presence of the imide compound to form the corresponding carboxylic acid. For example, diethylketone is oxidized to form acetic acid and propionic acid, and cyclooctanone is oxidized to form suberic acid.

An amine is oxidized in the presence of the imide compound to form the corresponding Schiff base, oxime, etc.

A heterocyclic compound is oxidized to form the corresponding alcohol, ketone or carboxylic acid. For example, the heterocyclic compound (a) exemplified in the item of the substrate is oxidized to form the corresponding compound having a carbonyl group by converting a methylene group adjacent to a heteroatom (e.g., oxygen, sulfur, or nitrogen atom) to a carbonyl group in the non-aromatic heterocyclic ring. In the case of oxidizing the heterocyclic compound (b), a compound having a methyl group adjacent to an aromatic heterocycle is oxidized to form the corresponding heterocyclic aldehyde or heterocyclic carboxylic acid, and a compound having a methylene group adjacent to an aromatic heterocycle is oxidized to form the corresponding heterocyclic ketone.

Such oxidation reaction is usually carried out in an atmosphere of oxygen. The oxygen source is not particularly restricted to a specific one, and pure oxygen or oxygen diluted with an inert gas such as nitrogen, helium, argon, or carbon dioxide may be employed. From the viewpoints of not only operability and safety but also economy, air is preferably used. The amount of oxygen can be selected according to the species of the substrate, and is usually, relative to 1 mol of the substrate, 0.5 mol or more (e.g., about 1 mol or more), preferably about 1 to 100 mol, and more preferably about 2 to 50 mol. In many instances, the reaction is carried out under oxygen atmosphere containing an excess mole of oxygen.

When supplying the reactor with molecular oxygen, the reaction may be carried out in a closed system after supplying a reactor with sufficient molecular oxygen in advance, or with molecular oxygen flowing continuously. In the case of continuous flow of molecular oxygen, oxygen can be supplied in a flow rate which corresponds to the amount of oxygen.

Incidentally, when the oxidation reaction is carried out in the coexistence of an aldehyde (in particular, a $C_{1-6}$aldehyde such as acetoaldehyde), a ketone and/or an alcohol, the oxidation reaction is accelerated to produce an aliphatic dicarboxylic acid or an aromatic carboxylic acid with high efficiency. Moreover, a reaction is sometimes accelerated in the coexistence of a radical generator or a radical promoter.

(Other Reactions)

Further, in the presence of the imide compound, the substrate (e.g., a hydrocarbon) is reacted with (i) oxygen and carbon monoxide, (ii) a nitrogen oxide (e.g., NO, $NO_2$, $N_2O_3$), (iii) a sulfur oxide (e.g., $SO_2$), (iv) a vicinaldicarbonyl compound, or (v) a compound which is radically formable of a carbon-carbon bond to form (i) a carboxylic acid, (ii) a nitro compound, (iii) an organic sulfur-containing acid (e.g., sulfonic acid), (iv) an acylation reaction product (an aldehyde, a ketone), or (v) a carbon-carbon bond forming reaction product or a derivative thereof (e.g., an oxide, a cyclized product such as lactone), which corresponds to the substrate, respectively.

For example, in the presence of the imide compound, a bridged cyclic hydrocarbon having a tertiary carbon atom (methine carbon) is reacted with oxygen and carbon monoxide, a nitrogen oxide (e.g., NO, $NO_2$, $N_2O_3$), sulfur oxide (e.g., $SO_2$), 1,2-dicarbonyl compound, or a compound which is radically formable of a carbon-carbon bond to form a compound or a derivative thereof in which is introduced with a carboxyl group, a nitro group, a sulfonic acid group, an acyl group, a hydrocarbon group or the like into the tertiary carbon atom.

[Reaction Solvent]

The above-exemplified reaction may be carried out in the absence of a solvent inert to the reaction, but can be usually carried out in the presence of a solvent. Examples of the solvent are organic carboxylic acids such as formic acid, acetic acid, propionic acid, trichloroacetic acid and trifluoroacetic acid; hydrocarbons such as hexane, octane and benzene; halogenated hydrocarbons such as chloroform, dichloromethane, dichloroethane, carbon tetrachloride, dichlorobenzene and trifluoromethylbenzene; alcohols such as methanol, ethanol, propanol, butanol, octanol, 2-ethylhexanol; ketones such as acetone, methyl ethyl ketone and methyl isobutyl ketone; esters such as methyl acetate, ethyl acetate and butyl acetate; ethers such as dimethyl ether, diethyl ether and diisopropyl ether; nitro compounds such as nitrobenzene, nitromethane, and nitroethane; nitriles such as acetonitrile, propionitrile and benzonitrile; amides such as formamide, acetamide, dimethylformamide (DMF), and dimethylacetamide; water; and mixed solvents thereof.

Particularly, in the oxidation reaction, the solvent usually includes a carboxylic acid (e.g., acetic acid), a hydrocarbon, an alcohol (methanol, 2-ethylhexanol), a ketone, an ester, an ether, a nitro compound, a nitrile, an amide, a water-containing solvent (e.g., an organic acid aqueous solution such as an acetic acid aqueous solution). In many cases, the substrate may be used as a solvent. Incidentally, as the water-containing solvent, an aqueous solution may be used which contains the organic solvent with the high concentration (e.g., about 40 to 99% by weight, preferably about 60 to 95% by weight, in particular, about 80 to 95% by weight).

[Reaction Condition]

The reaction utilizing the imide compound of the formula (1) smoothly proceeds even under relatively mild conditions. The reaction temperature can be suitably selected according to the species of the imide compound, the reacting agent and the substrate, and is for example 0 to 300° C., preferably about 30 to 250° C., and more preferably about 40 to 200° C. Usually, the reaction is effected at a temperature of about 40 to 150° C. (e.g., about 50 to 100° C.).

Particularly, in the oxidation reaction, the reaction temperature is, for example, about 0 to 300° C., preferably about 15 to 250° C., and more preferably about 30 to 200° C. Usually, the reaction is effected at a temperature of about 50 to 190° C. (in particular, about 70 to 190° C.).

Moreover, the reaction may be effected under atmospheric pressure or under applied pressure. When conducting the reaction under applied pressure, the pressure is usually about 1 to 100 atm (e.g., 1.5 to 80 atm), preferably about 2 to 70 atm, and more preferably about 3 to 50 atm.

The reaction time (residence time inflow reactions) can be suitably selected within the range of, e.g., about 1 minute to 48 hours, preferably about 2 minutes to 24 hours, and more preferably about 5 minutes to 8 hours, depending on the reaction temperature and pressure. Further, the reaction time may be, for example, suitably selected within the range of, e.g., about 30 minute to 48 hours, preferably about 1 to 36 hours, and more preferably about 2 to 24 hours.

Incidentally, in the oxidation reaction, when the water content of the reaction system is controlled within the range of 30% by weight or less (e.g., about 0 to 30% by weight), preferably about 3 to 20% by weight (e.g., about 3 to 18% by weight), more preferably about 4 to 15% by weight (e.g., about 4 to 10% by weight) relative to the whole reaction system, the oxidation reaction can be accelerated, and the formation of by-products can be inhibited, so that a reaction product such as a carboxylic acid can be obtained in high yield.

The reaction operation can be carried out in a continuous system, a batch system, or a semi-batch system. Moreover, the reaction may be carried out by reactive distillation accompanied by removal of water, or by the reactive distillation involving employing a water-separating apparatus, such as a decanter. The reaction may be carried out in two or more steps. As reaction apparatus (reactor), use can be made of a conventional one, and a plurality of apparatuses may be used. When a plurality of apparatuses may be used, the apparatus may be connected in series and/or in parallel.

[Process for Separating the Imide Compound and the Reaction Product]

A variety of reaction products (e.g., an alcohol, an aldehyde, a ketone, a carboxylic acid) are formed in the reaction mixture obtained by the reaction (e.g., oxidation reaction). Further, the activity of the imide compound is deteriorated as the reaction proceeds, and the aforementioned deactivated catalyst is sometimes formed. Moreover, plural reaction products and plural imide compounds may be contained in the reaction mixture.

According to the present invention, the reaction product and the imide compound (including the deactivated or decomposed product) are separated from the reaction mixture. The separating operation can be carried out by (A) crystallization [e.g., (A1) solvent-crystallization or repulp with use of a solvent for crystallization, (A2) cooling-crystallization] operation for separating the imide compound as a crystalline or non-crystalline component, or by (B) extraction operation for distributing the imide compound into a phase of the aqueous solvent with use of an aqueous solvent and a water-insoluble solvent. Incidentally, the reaction product and the imide compound may be separated by distillation operation according to their species.

[(A) Crystallization]

In the crystallization operation (A), the imide compound is separated as a crystalline or non-crystalline component by the solvent-crystallization (A1) or the cooling-crystallization (A2) according to the species of the reaction product and the imide compound.

(Solvent Crystallization Step A1)

In the separating process utilizing solvent-crystallization operation, the imide compound is crystallized with a solvent selected from a hydrocarbon, a chain ether and water from a reaction mixture containing the reaction product and the imide compound (including a decomposed product) and recovered in the form of solid. Thus, this process is advantageous for separating a compound soluble in the above solvent as the reaction product (e.g., oxidation reaction products of the alicyclic hydrocarbon and the alicyclic alcohol) and the imide compound insoluble in the above solvent (e.g., an aromatic imide compound).

The solvent for crystallization can be selected according to the species of the reaction product. When the reaction product is a low or weakly polar compound (such as an oxidation reaction product of a monocyclic $C_{4-16}$cycloalkane), it is preferred that a hydrocarbon or chain ether is employed as the solvent for crystallization. When the reaction product is a highly polar compound (e.g., a water-soluble compound; the oxidation product of a polycycloalkane having plural bridgeheads), it is preferred that water is employed as the solvent for crystallization.

In the present invention, examples of hydrocarbons which are employed for crystallization (or repulp) operation include, for example, aliphatic hydrocarbons having 4 to 20 (preferably 4 to 16, more preferably 5 to 12) carbon atoms such as pentane, hexane, isohexane, heptane, octane, isooctane, 2-ethylhexane and decane; alicyclic hydrocarbons having 4 to 20 (preferably 4 to 16, more preferably 5 to 12) carbon atoms such as cyclopentane, cyclohexane and cyclooctane; aromatic hydrocarbons having 6 to 12 (preferably 7 to 10) carbon atoms such as benzene, toluene, xylene and ethylbenzene.

Moreover, as the chain ether, there may be mentioned, for example, a $diC_{1-6}$alkyl ether such as diethyl ether, diisopropyl ether, t-butyl methyl ether and dibutyl ether; a $C_{1-6}$alkyl-$C_{6-10}$aryl ether such as anisol.

These solvents can be used singly or in combination. The particularly preferred solvent includes an aliphatic hydrocarbon having 4 to 12 carbon atoms such as hexane, an alicyclic hydrocarbon having 4 to 12 such as cyclohexane, a $diC_{1-4}$alkyl ether such as t-butyl methyl ether, and a mixed solvent thereof.

The amount to be used of the hydrocarbon, the chain ether or water employed in the crystallization or repulp operation varies according to the species of the operation (e.g., repulp or crystallization), the species and amounts of the reaction product and those of the imide compound, and can be suitably selected within the range of, for example, about 50 to 100,000 parts by weight and about 100 to 10,000 parts by weight relative to 100 parts by weight of the imide compound contained in the mixture.

Moreover, as long as the separation efficiency does not deteriorate, a solvent other than the hydrocarbon, the chain ether and water may be contained in the mixture (process liquid) which is subjected to the crystallization or repulp operation. For example, a reaction solvent or a solvent which has been employed in a separating or purifying operation such as extraction and crystallization before the crystallization or repulp operation of the present invention may be contained in the mixture (process liquid). Further, in order to improve the separating efficiently, the crystallization or repulp operation may be carried out by adding another solvent (e.g., in case of the hydrocarbon and the chain ether, an organic solvent compatible with the hydrocarbon or the chain ether; in case of water, an aqueous solvent) with the hydrocarbon, the chain ether or water.

Examples of such solvents include, for example, organic solvents such as acetic acid and propionic acid; nitriles such as acetonitrile, propionitrile and benzonitrile; amides such as N,N-dimethylformamide; halogenated hydrocarbons such as chloroform, dichloromethane, 1,2-dichloroethane, chlorobenzene and trifluoromethylbenzene; nitro compounds such as nitrobenzene and nitromethane; esters such as ethyl acetate, butyl acetate, methyl benzoate and ethyl benzoate; cyclic ethers such as tetrahydrofuran and dioxane; alcohols such as methanol, ethanol and isopropyl alcohol; ketones such as acetone and ethyl methyl ketone.

Incidentally, in order to separate the imide compound and the reaction product effectively, it is preferred in the crystallization (or repulp) operation that the amount (total amount) of the specific solvent (hydrocarbon, chain ether or water) contained in the reaction mixture is, for example, 50% by weight or more, in particular 70% by weight or more (especially 90% by weight or more) relative to the whole solvent (including a volatile component) in the reaction mixture.

The temperature for crystallization treatment varies according to the species of the treatments, and is usually the range of about −10° C. to +150° C., preferably about 0 to +100° C. The above treatment can be carried out in any manners such as batch manner and continues manner. The treatment may be once or plural times. When the treatments are carried out plural times, two or more different treatments may be combined. The crystallization can be carried out by cooling and/or condensing the solution. Incidentally, the repulp treatment can be carried out by stirring the mixture containing a solid and a liquid. The solid obtained by crystallization or repulp (imide compound) can be separated by utilizing a conventional solid-liquid separating means such as filtration and centrifugation. The separated imide compound can be reused as a catalyst without any treatment or after subjected to the suitable regenerating treatment. Moreover, the reaction product can be isolated by a conventional isolation and purification means such as condensation, crystallization, recrystallization, extraction, distillation, column chromatography from the filtrate (mother liquor) from which the imide compound has been separated.

An operating process for the solvent-crystallization (A1) is, for example, carried out (i) with use of the hydrocarbon, the chain ether or water as a reaction solvent (or excess of a reaction component) by composition-changing of a system during a reaction, or by cooling or condensing after completion of the reaction to crystallize the imide compound, or (ii) by adding the hydrocarbon, the chain ether or water into the reaction mixture (if necessary, after subjected to a suitable treatment such as filtration, condensation, evaporation to dryness, control of liquid property, extraction, washing and crystallization) to crystallize or repulp the imide compound.

As the concrete example of the embodiment (ii), the imide compound can be recovered as a crystalline component (solid) by filtrating off a participate from a reaction (e.g., oxidation reaction) mixture, condensing a filtrate, and adding a hydrocarbon or a chain ether (in case that the reaction product is non-polar compound), or water (in case that the reaction product is a polar compound) into a residue (condensate) to crystallize or repulp the imide compound.

Moreover, the imide compound may be recovered as a solid by condensing a reaction mixture (e.g., oxidation reaction), adding water to crystallize the reaction product and the imide compound, and adding a hydrocarbon or a chain ether into the resultant crystal to crystallize or repulp the imide compound.

Particularly, in the solvent crystallization step (A1), when the specific imide compound (inclusive of a decomposed product thereof) is a compound which tends to be soluble in a mild or moderate-polar solvent, and to be insoluble in an extremely low-polar or high-polar solvent, the imide compound can be efficiently separated and recovered as a solid by subjecting a mixture containing the reaction product and the imide compound to the crystallization step with the specific solvent. Therefore, there is no need to provide a solvent-removing step exceptionally, and the imide compound can be conveniently recovered. Thus, the process is advantageous from viewpoint of the cost.

(Cooling-Crystallization A2)

In the cooling-crystallization A2, the reaction product and the imide compound are separated from the reaction mixture by crystallizing the objective reaction product (objective compound) and distributing the imide compound into the non-crystalline component (a solvent phase).

The reaction product may be a reaction product crystallizable with a reaction solvent, and may be, for example, an alcohol derivative (e.g., an ester) or an aldehyde, but is usually an alcohol, a ketone, preferably a carboxylic acid. In particular, this process is advantageous for separating the imide compound and a water-insoluble compound (e.g., a compound which is in the form of solid at an ambient temperature (about 15 to 25° C.)), for example, a carboxylic acid [e.g., an aliphatic carboxylic acid having 6 or more (preferably 6 to 16, more preferably 6 to 12) carbon atoms, or an aromatic carboxylic acid (e.g., an aromatic polycarboxylic acid such as an aromatic dicarboxylic acid)], in particular, an aromatic carboxylic acid.

In the cooling crystallization step (A2), the reaction is carried out in the presence of a solvent, and a solvent which is a poor solvent for the reaction product and is a good solvent for the imide compound may be used. The reaction product and the imide compound are soluble in such a solvent as a reaction solvent at a reaction temperature. By utilizing such a solvent, the reaction product can be crystallized by cooling from the reaction mixture, and the imide compound can be distributed into the solvent phase.

As the reaction solvent, there may be mentioned the above exemplified solvent [e.g., a carboxylic acid (e.g., acetic acid), a hydrocarbon, an alcohol (e.g., methanol, 2-ethylhexanol), a ketone, an ester, an ether, a nitro compound, a nitrile, an amide, a water-containing solvent (e.g., an organic carboxylic aqueous solution such as acetic acid aqueous solution)]. In particular, in case that the objective compound is a water-insoluble carboxylic acid [in particular, an aliphatic carboxylic acid having 6 or more (preferably 6 to 12) carbon atoms or an aromatic carboxylic acid], the water-insoluble carboxylic acid can be efficiently crystallized from the reaction mixture by using a lower carboxylic acid (a $C_{1-4}$alkanecarboxylic acid such as acetic acid, in particular a water-soluble carboxylic acid), an alcohol (e.g., a $C_{1-10}$alcohol such as methanol, 2-ethylhexanol), or a water-containing solvent as a reaction solvent.

The cooling crystallization can be carried out by cooling the reaction mixture or the mixed solution, which contains the objective compound and the crystallization solvent (reaction solvent) and is heated to a suitable temperature (e.g., about 40 to 200° C.), to about −10° C. to 150, preferably about 0 to 100° C., more preferably about 10 to 80° C., in particular around a room temperature.

Incidentally, if necessary, a solvent which is a poor solvent for the reaction product and is a good solvent for the imide compound (e.g., an alcohol) may be added to the reaction mixture after completion of reaction or after condensation of the crude reaction mixture.

In the preferred embodiment of the present invention, it is suitable for separating a water-insoluble carboxylic acid as an objective compound (a $C_{6-10}$aliphatic carboxylic acid such as adipic acid; an aromatic carboxylic acid such as benzenecarboxylic acid and a heterocyclic carboxylic acid) and the aromatic imide compound with, as a reaction solvent, a $C_{1-4}$alkanecarboxylic acid (in particular, a $C_{2-3}$alkanecarboxylic acid such as acetic acid), an alcohol (a $C_{1-10}$alkyl alcohol), a mixed solvent thereof, or a water-containing solvent thereof.

Incidentally, in the crystallization operation (A) (the solvent-crystallization step A1 and cooling crystallization step A2), when the reaction is carried out in the presence of a solvent, a reaction mixture may be condensed before the crystallization step (A1) or (A2) in order to improve the crystallization efficiency, or the reaction mixture may be subjected to the crystallization step without condensation. Moreover, a non-crystalline or crystalline component containing the objective compound and a crystalline component or a solvent phase (a non-crystalline component) containing the imide compound can be separated by the simple means such as filtration, decantation, and centrifugation. The crystalline component may be, if necessary, purified by washing, recrystallization (crystallization), extraction and the like. Further, the reaction product or the imide compound may be separated from the non-crystalline component by distribution (e.g., extraction), crystallization, filtration (e.g., filtration and washing), adsorption, distillation, drying or combination of these operations. The imide compound may be recycled to the reaction system, if necessary after regeneration. The aftermentioned method may be used as the regeneration method.

[(B) Extraction]

In the process comprising the extraction step (B), by extraction operation with an aqueous solvent containing at least water and a water-insoluble solvent separable from the aqueous solvent, the reaction product and the imide compound (including the deactivated or decomposed product) are distributed into a phase of the water-insoluble solvent and a phase of the aqueous solvent, respectively. Therefore, the process is advantageous for the case that the reaction product is water-insoluble compound (e.g., a cyclic alcohol, a cyclic ketone, an aldehyde having a cyclic hydrocarbon group, a carboxylic acid having a cyclic hydrocarbon group).

Moreover, as the imide compound, an imide compound which has high affinity and extraction ability to an aqueous solvent [e.g., an imide compound derived from an aliphatic polycarboxylic anhydride] is preferred. However, in even case of a water-insoluble imide compound [an imide compound derived from an alicyclic polycarboxylic anhydride or an aromatic polycarboxylic anhydride], such an imide compound can be efficiently separated by selecting an extraction solvent, and further, as aftermentioned, can be converted by hydrolysis into a compound which is water-soluble and is easy to regenerate to the imide compound, and thus such an imide compound is suitable for the catalyst.

(Aqueous Solvent Containing at Least Water)

As the aqueous solvent containing at least water, an aqueous solvent which contains water as a main component can be employed. The aqueous solvent includes a mixed solvent containing water and the other water-soluble organic solvent (e.g., a $C_{1-3}$alcohol such as methanol, a ketone such as acetone, an ether such as dioxane and tetrahydrofuran, a lower aliphatic carboxylic acid such as acetic acid). The content of the organic solvent in the mixed solvent is, for example, about 0 to 60% by weight (usually about 0 to 25% by weight) relative to water. As the preferred aqueous solvent, water is exemplified.

Incidentally, an aqueous solvent containing a base may be employed as an aqueous solvent. When the aqueous solvent containing a base is employed, among the imide compounds, an acidic compound, for example, an imide compound having the unit shown by the formula (1) wherein X is hydroxyl group, and an imide compound having the unit shown by the formula (4) wherein Y is hydrogen atom form the corresponding salts so that imide compounds are efficiently distributed into the phase of the aqueous solvent. For example, when N-hydroxyphthalimide is employed in a reaction as the imide compound, by using the aqueous solvent containing a base as the aqueous solvent in the distribution (extraction) operation after the reaction, the residual N-hydroxyphthalimide and phthalimide which is deactivated product of N-hydroxyphthalimide form the respective corresponding salts to be distributed into the phase of the aqueous solvent.

Moreover, to the reaction mixture is added the aqueous solvent containing at least base and, for example, heated to hydrolyze, and the reaction mixture is separated into two liquid phases so that the residual imide compound of the formula (1), compounds having the units shown by the formulae (4) and (5) which are deactivated product of the imide compound and ring-opened derivatives thereof are converted into a salt of a dicarboxylic acid having the unit shown by the following formula (3).

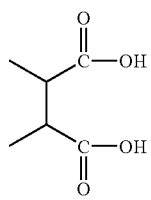

(3)

Therefore, the imide compound which has been employed in the reaction can be distributed into the phase of the aqueous solvent in the form of the dicarboxylic acid salt with extremely efficient. For example, when N-hydroxyphthalimide is employed in a reaction as the imide compound, in the extraction operation after the reaction, the reaction mixture is hydrolyzed with the aqueous solvent containing a base so that almost N-hydroxyphthalimide and a deactivated thereof are converted into phthalic acid salts to be distributed into the phase of the aqueous solvent. Incidentally, in the present invention, the hydrolysis treatment with such an aqueous solvent is included in the extraction operation. The deactivated imide compound subjected to hydrolysis treatment is suitably used in the aftermentioned regeneration method of the imide compound.

As the base, an inorganic base or an organic base may be employed. The inorganic base includes, for example, ammonia; an alkali metal hydroxide such as sodium hydroxide and potassium hydroxide; an alkali metal hydrogencarbonate such as sodium hydrogencarbonate and potassium hydrogencarbonate; an alkali metal carbonate such as sodium carbonate and potassium carbonate; an alkaline earth metal hydroxide such as calcium hydroxide; an alkaline earth metal carbonate such as calcium carbonate. The organic base includes, for example, an amine [an aliphatic amine such as dimethylamine, diethylamine, trimethylamine, methylenediamine and ethylenediamine, an aromatic amine such as N,N-dimethylaniline, a cyclic amine such as morpholine, piperidine and pyrrolidine]; a basic nitrogen-containing heterocyclic compound such as pyridine; an alkali metal alkoxide such as sodium methoxide and sodium ethoxide.

(Water-Insoluble Solvent)

A water-insoluble solvent employed in the extraction may be liquid-separable from the aqueous solvent. The water-insoluble solvent includes, for example, a hydrocarbon (e.g., an aliphatic hydrocarbon, an alicyclic hydrocarbon, an aromatic hydrocarbon, a halogenated hydrocarbon), an alcohol, a ketone, an ester, a nitro compound, a nitrile, an ether and a mixed solvent thereof, and can be suitably selected according to the species of the reaction product and the imide compound. These hydrophobic (water-insoluble) solvents may be added after completion of reaction, and may be employed as a reaction solvent.

When the hydrophobic solvent is employed as a reaction solvent, it can be employed as the liquid-separable solvent from the aqueous solvent after completion of reaction. Moreover, when a hydrophobic substrate (e.g., a hydrocarbon, a ketone) is employed as a substrate, the substrate is employed as a reaction solvent, so that the residual substrate can be employed as a liquid-separable solvent from the aqueous solvent after completion of reaction.

Among the hydrocarbons, the aliphatic hydrocarbon includes, for example, an aliphatic hydrocarbon having 5 to 15 carbon atoms such as pentane, hexane, isohexane, heptane, isoheptane, octane, isooctane and decane. The preferred aliphatic hydrocarbon includes a hydrocarbon having 5 to 12 (in particular 6 to 10) carbon atoms. The alicyclic hydrocarbon includes, for example, an alicyclic hydrocarbon having 5 to 15 carbon atoms such as cyclopentane, cyclohexane, methylcyclohexane, dimethylcyclohexane, ethylcyclohexane, cycloheptane and cyclooctane. The preferred alicyclic hydrocarbon includes an alicyclic hydrocarbon having 5 to 12 carbon atoms. The aromatic hydrocarbon includes, for example, an aromatic hydrocarbon having 6 to 12 carbon atoms such as benzene, toluene, ethylbenzene, cumene, (o-, m-, p-)xylene and p-t-butyltoluene. The halogenated hydrocarbon includes, for example, chloromethane, dichloromethane, chloroform, carbon tetrachloride, dichlorofluoromethane (Freon), dichloroethane, trichloroethylene, dichloropropane, dichloropentane, chlorobenzene, dichlorobenzene and trichlorobenzene.

The alcohol includes an alcohol derivative of the aforementioned hydrocarbon, and includes, for example, an aliphatic alcohol, an alicyclic alcohol and an aromatic alcohol. As the aliphatic alcohol, there may be mentioned, for example, an aliphatic monoalcohol having 4 to 15 carbon atoms such as butanol, heptanol, hexanol, methylhexanol, ethylhexanol, heptanol, octanol, decanol. As the alicyclic alcohol, there may be mentioned, for example, an alicyclic alcohol having 5 to 15 carbon atoms such as cyclohexanol, methylcyclohexanol, ethylcyclohexanol, cycloheptanol and cyclooctanol. As an aromatic alcohol, there may be mentioned, for example, an aromatic alcohol having 6 to 12 carbon atoms such as benzylalcohol and phenethyl alcohol.

The ketone includes a ketone derivative of the aforementioned hydrocarbon, and includes, for example, a chain ketone and a cyclic ketone. As the chain ketone, there may be mentioned, for example, an aliphatic ketone having 4 to 15 carbon atoms such as methyl ethyl ketone, methyl isobutyl ketone and diisobutyl ketone. Moreover, as the cyclic ketone, there may be mentioned, for example, a cyclic ketone having 5 to 15 carbon atoms such as cyclohexanone, methylcyclohexanone, cycloheptanone and cyclooctanone.

As the ester, there may be mentioned, an ester compound having 3 to 20 carbon atoms, for example, a $C_{2-10}$aliphatic carboxylic acid-$C_{1-10}$alkyl ester such as methyl acetate, ethyl acetate, propyl acetate, isopropyl acetate, butyl acetate, hexyl acetate, amyl acetate, isoamyl acetate, 2-ethylhexyl acetate, methyl propionate, ethyl propionate, butyl propionate, hexyl propionate, amyl propionate, ethyl valerate, ethyl hexanoate, ethyl heptanoate, ethyl octanoate and ethyl decanoate; a $C_{2-4}$aliphatic carboxylic acid-$C_{5-10}$cycloalkyl ester such as cyclohexyl acetate and cyclooctyl acetate; an aryl ester such as phenylacetate and phenylpropionate; a $C_{7-12}$aromatic carboxylic acid-$C_{1-10}$alkyl ester such as methyl benzoate, ethylbenzoate, butylbenzoate, dimethylphthalate, diethyl phthalate and dibutyl phthalate.

As the nitro compound, there may be mentioned a nitro compound having 2 to 10 carbon atoms, for example, an aliphatic nitro compound such as nitroethane, nitropropane and nitropentane; an aromatic nitro compound such as nitrobenzene, dinitrobenzene, nitrotoluene and nitroxylene.

As the nitrile, there may be mentioned a nitrile having 7 to 12 carbon atoms, for example, a $C_{7-12}$aromatic nitrile such as benzonitrile.

As the ether, there may be mentioned, for example, a chain ether such as diethyl ether, diisopropyl ether, dipropyl ether, dibutyl ether, t-butyl methyl ether and anisol.

The preferred water-insoluble solvent includes, for example, a hydrocarbon, a ketone, an ester, a nitrile and an ether. Especially, a hydrocarbon having 5 to 15 carbon atoms (e.g., hexane, cyclohexane, toluene), a ketone having 4 to 15 carbon atoms (e.g., methyl ethyl ketone, cyclohexanone), an ester compound having 3 to 20 carbon atoms (e.g., ethyl acetate, phenyl acetate, methyl benzoate), a nitrile having 7 to 12 carbon atoms (e.g., benzonitrile) and an ether having 4 to 12 carbon atoms. The particularly preferred water-insoluble solvent includes an aliphatic or alicyclic hydrocarbon having 5 to 12 carbon atoms and an ether having 4 to 12 carbon atoms.

(Extraction Operation)

The extraction can be carried out by adding the aqueous solvent and the water-insoluble solvent to the reaction mixture after completion of reaction or its product resulted from a treatment (e.g., a mixture subjected to the treatment such as condensation, filtration, extraction, distillation and crystallization), if necessary, subjecting to hydrolyze by heating or the like, followed by mixing by stirring or the like to liquid-separate. Incidentally, when the hydrolysis treatment is carried out, the water-insoluble solvent may be added after the hydrolysis treatment.

Incidentally, when the reaction product contains an acidic compound such as a carboxylic acid, the aqueous solvent containing a base is employed for the extraction, so that it tends to be difficult to separate the reaction product, the imide compound (e.g., an imide compound of the formula (2) wherein $R^1$ and $R^2$ bond each other to form an aromatic or non-aromatic ring having 5 to 12 members), deactivated catalyst and/or a hydrolyzed product thereof. In such case, after the acidic compound such as dicarboxylic acid of the reaction product is recovered by a suitable method (e.g., crystallization, distillation), the other reaction product, the imide compound, the deactivated catalyst and/or a hydrolyzed product thereof may be separated.

The ratio of the hydrophilic solvent and the hydrophobic (water-insoluble) solvent can be suitably selected according to the species of the reaction products, the imide compound catalyst and its deactivated, and is, for example, the former/the latter (weight ratio)=about 0.01/1 to 10/1, preferably about 0.05/1 to 5/1, more preferably about 0.1/1 to 3/1, and usually about 0.2/1 to 2/1.

The extraction may be carried out in whichever a batch manner or continues manner, and may be carried out in multistage operations, if necessary. The extraction number of the reaction mixture with use of the hydrophilic solvent and the hydrophobic solvent can be suitably selected according to the species of the oxidation reaction product and the oxidation catalyst, and is, for example, about 1 to 5 times, usually about 1 to 3 times.

The pH of the extraction system can be suitably selected within the wide range depending on the species of the reaction product, the imide compound catalyst and the deactivated catalyst, and is, for example, about 5 to 10, preferably about 6 to 8. When the catalyst or the deactivated catalyst (including the hydrolyzed product) is recovered in the form of salt, pH may be more than 10.

When a solvent containing a base is employed as the aqueous solvent, the amount of the base is, for example, 1 equivalent or more (e.g., about 1 to 20 equivalents), preferably about 1 to 10 equivalents, more preferably about 1 to 5 equivalents relative to 1 equivalent of the imide compound catalyst employed in a reaction.

In the present invention, the extraction may be carried out with warming, the extraction temperature is, for example, about 0 to 200° C., preferably about 5 to 150° C., more preferably about 10 to 130° C., and the extraction is usually carried out at about 15 to 100° C. Particularly, when the hydrolysis treatment is carried out with the aqueous solvent containing a base, it is preferred that the extraction is carried out with warming for the purpose of efficient progress of the hydrolysis. In this case, liquid-separation may be carried out after the temperature lowers. If necessary, in order to improve the extraction efficiency, the extraction may be effected under applied shearing stress, and may be effected under atmospheric pressure or under applied pressure.

By the extraction operation, the reaction product having a hydrophobic group and the imide compound can be separated by distributing the phase of the hydrophobic organic solvent and the phase of the aqueous solvent, respectively.

Incidentally, the imide compound (inclusive of the deactivated catalyst) is recovered from the aqueous solvent phase (in case of salt, followed by liberation) to recycle or reuse into the reaction system. Moreover, the deactivated or a salt thereof distributed into the aqueous solvent phase can be converted into the imide compound of the formula (1) by reacting with hydroxylamine or an acid if necessary, after hydrolysis with an acid or an alkali, ring-closing reaction, ring-opening reaction, liberation, and the like. Further, the dicarboxylic acid salt of the formula (3) distributed into the aqueous solvent phase can be converted into the imide compound of the formula (1) by reacting with hydroxylamine, if necessary, after liberation. An imide compound regenerated thereby can be recycled and reused to the reaction system. Furthermore, the co-catalyst may be separated and recovered by the extraction operation to recycle and reuse into the reaction system. Incidentally, the after-mentioned regeneration method may be utilized as the regeneration of the imide compound.

Incidentally, the above Japanese Patent Application Laid-Open No. 114702/1998 (JP-A-10-114702) does not disclose about a deactivated catalyst, but the process disclosed in the literature can be adopted to the case that the deactivated catalyst exists. For example, when the reaction product is an extremely high-polar compound such as adipic acid, by suitably selecting an extraction solvent, the reaction product can be distributed into the aqueous solvent phase, and the imide compound catalyst and/or the deactivated catalyst are/is distributed into the water-insoluble solvent phase.

[Distillation]

In the present invention, the reaction product and the imide compound may be separated from the reaction mixture by a distillation operation.

The distillation is usually carried out by using a distilling column. The number of plates of the distilling column may for example be about 1 to 100, preferably about 5 to 80, more preferably about 10 to 70, and particularly about 10 to 60. The distilling operation may be conducted at an overhead temperature of about −20° C. to 300° C. (preferably about 0 to 250° C., more preferably about 20 to 200° C., and particularly about 40 to 200° C.), a bottom temperature of about 20 to 400° C., preferably about 30 to 300° C. and more preferably about 50 to 250° C. and at a pressure of about 0.13 kPa to 2 MPa, preferably about 1.3 kPa to 1 MPa, depending on the species of a lower-boiling point component (e.g., a reaction product) and a higher-boiling point component (e.g., an imide compound). Moreover, the distilling operation can be conducted by refluxing the distillate at a suitable reflux ratio (e.g., about 0.01 to 50, preferably about 0.1 to 40, more preferably about 1 to 30).

The distillation may be conducted with an evaporator. The evaporation operation can be conducted, for example, at a pressure of about 0.13 kPa to 2 MPa, preferably about 1.3 kPa to 1 MPa, and at a temperature of about −20° C. to 300° C., preferably about 0 to 250° C., more preferably about 20 to 250° C., and particularly about 40 to 200° C.

The process is advantageous for the case that the difference between a boiling point of the imide compound and that of the reaction product is large.

[Separation of a Component Other than the Imide Compound and the Reaction Product]

The reaction mixture sometimes contains a raw material for reaction (substrate), a reaction solvent, a co-catalyst such as a metal catalyst, a by-product [a lower carboxylic acid than the objective compound or derivatives thereof (e.g., esters)], a reaction promoter, a solvent employed in a purification step, as well as the reaction product and the imide compound (including the deactivated catalyst). Therefore, in the separation processes (A) and (B) of the present invention, in order that each component or an impurity in the reaction mixture is previously removed, the reaction mixture may be subjected to conventional separating and purifying operation such as filtration, condensation, distillation, dilution, controlling the liquid property, extraction, washing, crystallization, drying, recrystallization, and column chromatography, followed by subjected to the separating operation (A) or (B).

Moreover, the reaction mixture obtained by the reaction may be subjected to the separation step (A) or (B) without any treatment. In this case, the unreacted raw material for reaction (substrate), the co-catalyst and by-products are distributed into a crystalline or non-crystalline component, or a hydrophobic organic solvent phase or an aqueous solvent phase, respectively, depending on each characteristic. The unreacted raw material for reaction and the co-catalyst distributed into each component or each phase can be recovered by the above conventional separation method.

In particular, among the by-products, a carboxylic acid precursor (e.g., an alcohol or a derivative thereof, a ketone, an aldehyde corresponding to the substrate) can be separated by distribution (extraction), crystallization, adsorption, hydrolysis, saponification, neutralization, distillation (e.g., evaporation), filtration (e.g., filtration and washing), drying or a combination of these operations, if necessary to recycle to the reaction system.

Moreover, from the reaction mixture, the metal catalyst may be separated by a conventional method such as filtration (e.g., filtration and washing), removing a solvent, condensation, drying, or a combination of these operations. Further, the reaction mixture is subjected to adsorption treatment with an ion-exchange resin or the like, and the metal catalyst may be eliminated, regenerated and recycled to the reaction system. Incidentally, when a water-soluble co-catalyst (e.g., a salt of acetic acid) is employed, the metal catalyst is extracted with water from the reaction mixture to recycle without any treatment, or to recycle after regeneration in the form of carbonate or acetate. Moreover, after burning to ashes, the metal component may be recovered, regenerated and recycled to the reaction system.

Incidentally, by the aftermentioned processes (C)(D)(E), the metal catalyst may be separated from the reaction mixture prior to the separation operations (A) (B), or the metal catalyst may be separated from the product resulted from the separating operations (A)(B).

[Separating the Imide Compound and the Metal Catalyst]

In another process of the present invention, the imide compound and the metal catalyst can be separated from a mixture containing the imide compound and the metal catalyst. The mixture may be a reaction mixture obtained by the reaction (e.g., oxidation reaction).

The above separating operation can be carried out by (C) solvent-crystallizing step for crystallizing the imide compound with a solvent for crystallization, (D) adsorption step for adsorbing the metal catalyst by adsorption treatment, or (E) extraction step for using an aqueous solvent containing at least water and a water-insoluble separable from the aqueous solvent to distribute the imide compound and the metal catalyst into the phase of the water-insoluble solvent and the phase of the aqueous solvent, respectively.

[Solvent-Crystallization Step (C)]

In the solvent crystallization step (C), the imide compound and the metal catalyst are separated from the mixture by crystallizing the imide compound with a solvent for crystallization.

As the solvent for crystallization, a variety of solvents (extraction solvent) such as a hydrophobic solvent can be employed depending on the solubility characteristics of the metal catalyst. In many cases, the metal catalyst is extracted or separated with an aqueous solvent. As the aqueous solvent, water or a mixed solvent of water and a water-soluble solvent may be employed. As the water-soluble solvent, there may be mentioned the above exemplified aqueous solvent, for example, a carboxylic acid (e.g., a $C_{2-3}$alkanecarboxylic acid such as acetic acid), an alcohol (e.g., a $C_{1-4}$alkylalcohol such as methanol, ethanol and isopropanol), a ketone, a nitrile, an amide. These water-soluble solvents can be used singly or in combination. Incidentally, as a mixed solvent containing water, a mixed solvent containing water in proportion of, for example, about 5 to 95% by weight, preferably about 25 to 90% by weight, and in particular about 30 to 90% by weight can be employed. As the aqueous solvent, water is usually used.

The separating process utilizing the solvent-crystallization step (C) is advantageous for the case that the imide compound is an aromatic imide compound and the metal catalyst is a compound soluble in the aqueous solvent (in particular, a water-soluble metal catalyst such as a salt of acetic acid and a complex).

The imide compound and the metal catalyst separated by the crystallization treatment may be recycled to the reaction system. Moreover, the imide compound and the metal catalyst may be, if necessary, regenerated and recycled to the reaction system.

Incidentally, the non-crystalline component (the aqueous solvent phase) containing the metal catalyst may be recycled to the reaction system without any treatment, or the metal catalyst or the metal component may be recovered from the non-crystalline component, if necessary to regenerate and recycle to the reaction system. For example, the metal catalyst or the metal component recovered may be, if necessary, regenerated in the form of carbonate or acetate, or after burning to ashes, it may be recovered, regenerated, and recycled to the reaction system. The recover of the metal catalyst or the metal component can be carried out by a conventional method such as crystallization, filtration (filtration and washing), adsorption (e.g., adsorption and elimination with an ion-exchange resin or the like), removing a solvent or condensation, drying and a combination of these methods.

[Adsorption Step (D)]

In the adsorption step (D), the imide compound and the metal catalyst are separated from the mixture by the adsorption operation. This process is not particularly limited to a specific one, and is advantageous for separating a hydrophobic imide compound and a water-soluble metal catalyst.

In the adsorption step, a variety of adsorbents, for example, activated carbon, zeolite, silica, silica gel, silica-alumina, titania and magnesia can be used. The specific surface area of the porous adsorbent may be, for example, about 10 to 5,000 $m^2/g$, preferably about 50 to 4,000 $m^2/g$ and more preferably about 100 to 3,500 $m^2/g$. The preferred adsorbent includes an ion exchanger, for example, an inorganic ion exchanger (e.g., an ion exchanger having a non-layer structure such as zeolite, silica, and silica-alumina; an ion exchanger having a layer structure such as tetrasilicic mica, montmorillonite, hectorite, synthesized fluorine lithium-containing taenilolite, synthesized fluorine-containing hectorite, metal salt of phosphoric acid), an organic ion exchanger (e.g., an anion exchange resin, for example, a strong-basic ion exchange resin having a quaternary ammonium base (e.g., trimethylammonium base, dimethylethanolammonium base), a weak-basic ion exchange resin having a primary, secondary or tertiary amino group; a cation exchange resin, for example, a strong-acidic ion exchange resin having a sulfonic acid group, a super-acidic ion exchange resin having an alkyl fluoride sulfonic acid group, a weak-acidic ion exchange resin having a carboxyl group, a phosphonic acid group or a phosphinic acid group; chelating resin, for example, an imidinoacetic acid-typed chelating resin, polyamine-typed chelating resin; a resin having an acidic group and a basic group (snake-cage resin)).

In the ion exchanger, the ion exchange capacity can be suitably selected, and may be, for example, about 1 to 5 meq/ml (dry resin). The ion exchanger may be whichever of gel-type or porous-type. Among the ion exchangers, the ion exchange resin may have a crosslinked structure, if necessary.

As the adsorption operation with the adsorbent, there may be mentioned a variety of methods which comprise contacting a treated liquid containing at least metal catalyst [in particular, a treated liquid containing the imide compound and the metal catalyst (especially an aqueous solvent)] with the adsorbent, for example, a method which comprises conducting the adsorption treatment by adding the adsorbent to the treated liquid, a method which comprises conducting the adsorption treatment by passing the treated liquid through a treatment apparatus such as a column containing the adsorbent. The adsorbent treatment condition (e.g., the amount of the adsorbent, the flow amount of the treated liquid) can be selected depending on the adsorption characteristic of the adsorbent, for example, the temperature of the adsorbent treatment is usually about 10 to 50° C.

The imide compound and the metal catalyst separated by the adsorption treatment may be recycled to the reaction system. Moreover, the imide compound and the metal catalyst is, if necessary regenerated and recycled to the reaction system. For example, the metal catalyst or the metal component recovered may be, if necessary, regenerated in the form of carbonate or acetate, or after burning to ashes, it may be recovered, regenerated, and recycled to the reaction system.

[Extraction Step (E)]

In the process comprising the extraction step (E), the imide compound (including the deactivated or decomposed product) and the metal catalyst are subjected to the extraction operation with an aqueous solvent containing at least water and a water-insoluble solvent separable from the aqueous solvent to distribute the imide compound and the metal catalyst into the phase of the water-insoluble solvent and the phase of the aqueous solvent, respectively.

Thus, the process is advantageous for the case that the imide compound is a water-insoluble compound (e.g., an aromatic imide compound) and the metal catalyst is a water-soluble compound.

(Aqueous Solvent Containing at Least Water)

As the aqueous solvent containing at least water, an aqueous solvent which contains water as a main component can be employed. The aqueous solvent includes a mixed solvent containing water and the other water-soluble organic solvent (e.g., a $C_{1-3}$alcohol such as methanol, a ketone such as acetone, an ether such as dioxane and tetrahydrofuran, a lower aliphatic carboxylic acid such as acetic acid). The content of the organic solvent in the mixed solvent is, for example, about 0 to 60% by weight (usually about 0 to 25% by weight), preferably about 0 to 10% by weight relative to water. As the preferred aqueous solvent, water is exemplified.

(Water-Insoluble Solvent)

A water-insoluble solvent employed in the extraction may be liquid-separable from the aqueous solvent. The water-insoluble solvent includes, for example, the above exemplified water-insoluble solvent [for example, an aliphatic hydrocarbon (e.g., a hydrocarbon having 5 to 12 carbon atoms such as hexane), an alicyclic hydrocarbon (e.g. an alicyclic hydrocarbon having 5 to 15 carbon atoms such as cyclohexane), an aromatic hydrocarbon (e.g., an aromatic hydrocarbon having 6 to 12 carbon atoms such as p-t-butyltoluene and xylene), a halogenated hydrocarbon (e.g., dichloromethane), an alcohol (an aliphatic primary alcohol having 4 to 15 carbon atoms such as butanol and hexanol, an alicyclic alcohol having 5 to 15 carbon atoms such as cyclohexanol, an aromatic alcohol having 6 to 12 carbon atoms such as benzylalcohol), a ketone (an aliphatic ketone having 4 to 15 carbon atoms such as methyl ethyl ketone, a cyclic ketone having 5 to 15 carbon atoms such as cyclohexanone), an ester (e.g., a $C_{2-10}$aliphatic carboxylic acid-$C_{1-10}$alkyl ester such as methyl acetate, a $C_{2-4}$aliphatic carboxylic acid-$C_{5-10}$cycloalkyl ester such as cyclohexyl acetate, an aryl ester such as phenyl acetate, a $C_{7-12}$aromatic carboxylic acid-$C_{1-10}$alkyl ester such as methyl benzoate), a nitro compound (e.g., a nitro compound having 2 to 10 carbon atoms), a nitrile (e.g., a nitrile having 7 to 12 carbon atoms), an ether (e.g., a chain ether such as dibutyl ether) and a mixed solvent thereof]. The water-insoluble solvent can be suitably selected according to the species of the imide compound. These hydrophobic (water-insoluble) solvents may be added to the reaction mixture after completion of reaction, and may be employed as a reaction solvent.

The preferred water-insoluble solvent includes, for example, a hydrocarbon (an aliphatic or alicyclic hydrocarbon having 6 or more carbon atoms, an aromatic hydrocarbon), an alcohol (an aliphatic alcohol having 4 or more carbon atoms), a nitrile (e.g., an aromatic nitrile) and a mixed solvent thereof. The particularly preferred water-insoluble solvent includes an alcohol separable from water (an alcohol having 4 to 12 carbon atoms), the alcohol and a hydrocarbon (an aliphatic hydrocarbon having 6 to 12 carbon atoms), a nitrile (e.g., aromatic alcohol) and the like.

When the hydrophobic solvent is employed as a reaction solvent, the hydrophobic solvent can be employed as a liquid-separable solvent from the aqueous solvent after completion of reaction. Further, when a hydrophobic substrate (e.g., a hydrocarbon, a ketone) is employed as a substrate, the substrate is employed as a reaction solvent, and after completion of reaction, the residual substrate can be employed as a liquid-separable solvent from the aqueous solvent.

(Extraction Operation)

The extraction operation is carried out in a similar manner to the operation described in the item of the process for separating the imide compound and the reaction product. That is, the extraction can be carried out by adding the aqueous solvent and the water-insoluble solvent to a mixture containing the imide compound and the metal catalyst or the reaction mixture obtained by reacting the substrate in the presence of a reaction system containing the imide compound and the metal catalyst or its treated product (e.g., a mixture resulted from the treatment such as condensation, filtration, extraction, distillation and crystallization), and mixing by stirring or the like to liquid-separate.

The ratio of the aqueous solvent and the hydrophobic (water-insoluble) solvent can be suitably selected according to the species of the imide compound and the metal catalyst, and is, for example, the former/the latter (weight ratio) =about 0.01/1 to 10/1, preferably about 0.05/1 to 5/1, more preferably about 0.1/1 to 3/1, and usually about 0.2/1 to 2/1.

The extraction may be carried out in whichever a batch manner or continuos manner, and may be carried out in multistage operations, if necessary. The extraction number of the reaction mixture with the hydrophilic solvent and the hydrophobic solvent is, for example, about 1 to 5 times, and usually about 1 to 3 times.

The extraction may be carried out with warming, the extraction temperature is, for example, about 0 to 200° C., preferably about 5 to 150° C. (e.g., about 15 to 150° C.), more preferably about 10 to 130° C., and in many cases, the extraction is usually carried out at about 15 to 100° C. If necessary, in order to improve the extraction efficiency, the extraction may be effected under applied shearing stress, and may be effected under atmospheric pressure or under applied pressure.

By the extraction operation, the metal catalyst and the imide compound can be shifted into the aqueous solvent phase and the water-insoluble solvent phase, respectively to separate the imide compound and the metal catalyst. The imide compound and the metal catalyst separated may be recycled to the reaction system. Moreover, the imide compound and the metal catalyst may be, if necessary regenerated and recycled to the reaction system. The separated metal catalyst may be recycled to the reaction system without purification or after purifying by a conventional method.

[The Separation of a Component Other than the Imide Compound and the Metal Catalyst]

As mentioned above, the reaction mixture sometimes contains a raw material for reaction (substrate), a reaction solvent, a by-product, a reaction promoter, a solvent employed in a purification step, as well as the imide compound (including the deactivated catalyst) and the metal catalyst. Therefore, when the imide compound and the metal catalyst are separated from the reaction mixture, in order that each component or an impurity in the reaction mixture is previously removed, the reaction mixture may be subjected to a conventional separating operation such as filtration, condensation, distillation, extraction, crystallization, recrystallization, column chromatography, and a combination of these operations followed by subjecting to the separating step (C), (D) or (E). Moreover, when the reaction is carried out in the presence of a solvent, in order to improve the extraction efficiency, the reaction mixture may be condensed prior to the separating step (C), (D) or (E), or may be subjected to the crystallization step without condensation.

Moreover, the reaction mixture obtained by the reaction may be subjected to the separation step without purification. In this case, the unreacted raw material for reaction (substrate) and the reaction product are distributed into a crystalline or non-crystalline component, or a hydrophobic organic solvent phase or an aqueous solvent phase, respectively, depending on each characteristic. The reaction product, unreacted raw material for reaction, and the by-products distributed into each component or each phase can be recovered by the above conventional method.

[The Relationship Between the Separating Step (A) (B) and the Separating Step (C)(D)(E)]

The separating step (A) (B) for the imide compound and the reaction product may be carried out in combination of the separating step (C)(D)(E) for the imide compound and the metal catalyst, if necessary. Moreover, the separating step (A) and (B) may be combined each other, and the separating step (C), (D) and (E) may be combined each other.

[Regeneration of the Imide Compound]

The utilization of the imide compound in the reaction (e.g., oxidation reaction) sometimes results in inactivation of the imide compound to form a compound having the unit represented by the formula (4) or a ring-open derivative thereof, a ring-open derivative of the imide compound having the unit represented by the formula (1), a dicarboxylic acid or an acid anhydride thereof corresponding to the imide compound having the unit represented by the formula (5).

In order to regenerate such deactivated catalyst, the deactivated catalyst is subjected to a hydrolysis treatment to convert into a dicarboxylic acid or its salt shown by the following formula (3), followed by reacting the dicarboxylic acid or its salt, or a reactive derivative of the dicarboxylic acid with (i) hydroxylamine or (ii) O-substituted hydroxylamine and then treating with an acid to regenerate the imide compound.

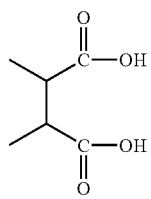

(3)

The regenerating method is applied to an deactivated catalyst resulted from change of at least part of the imide compound to an another compound (in particular, the compound of the formula (4) or a ring-open derivative thereof). Incidentally, when the dicarboxylic acid or its salt, or the reactive derivative of the dicarboxylic acid is formed as the deactivatd catalyst, or when the hydrolysis operation of the imide compound is carried out in the separating process (B), the imide catalyst can be regenerated by the operation (i) or (ii) without hydrolysis.

In the regenerating method, the reaction mixture containing the deactivated catalyst resulted from the reaction may be subjected to the regeneration of the catalyst without any treatment, or a system containing the deactivated catalyst (a catalyst mixture) may be subjected to the regeneration step of the catalyst after separating the reaction product and/or the metal catalyst from the reaction mixture by the above separation process, or after separating a by-product, a solvent, a insoluble material or the like by a conventional separation means such as filtration, condensation, distillation, extraction, crystallization. Moreover, when part of the imide compound is deactivated or modified, the deactivated catalyst and the activated catalyst are separated each other and the only deactivated catalyst may be subjected to the regeneration treatment or a mixture of the deactivated catalyst and the activated catalyst may be subjected to the regeneration of the catalyst.

The hydrolysis treatment can be carried out by a general hydrolysis method such as an alkali-hydrolysis and an acid-hydrolysis. As a base to be used in the alkali-hydrolysis, there may be mentioned the above exemplified base [e.g., an alkali metal hydroxide such as lithium hydroxide, sodium hydroxide and potassium hydroxide; an alkali metal carbonate such as lithium carbonate, sodium carbonate and potassium carbonate; an alkali metal hydrogencarbonate such as lithium hydrogencarbonate, sodium hydrogencarbonate and potassium hydrogencarbonate; an alkaline earth metal hydroxide such as magnesium hydroxide and calcium hydroxide; ammonia; an organic base such as triethylamine and pyridine].

As an acid to be used in the acid-hydrolysis, there may be mentioned, for example, an inorganic acid such as hydrogen fluoride, hydrogen chloride, hydrogen bromide, hydrofluoric acid, hydrochloric acid, hydrobromic acid, sulfuric acid, nitric acid and phosphoric acid; an sulfonic acid such as benzenesulfonic acid, p-toluenesulfonic acid and methanesulfonic acid.

The amount of the base or the acid is about 2 or more equivalents (e.g., about 2 to 20 equivalents), preferably about 2 to 10 equivalents, and more preferably about 2 to 5 equivalents relative to 1 equivalent (1 mol) of the catalyst (the deactivated catalyst or the total amount of the deactivated catalyst and the activated catalyst). Incidentally, when the acid is employed, the acid may be used in the catalytic amount. The amount of water to be used in the hydrolysis is usually 2 or more equivalents relative to 1 equivalent (1 mol) of the catalyst (the deactivated catalyst or the total amount of the deactivated catalyst and the activated catalyst), and in many cases, water is employed in large excess.

The hydrolysis temperature can be suitably selected depending on the species of the deactivated catalyst and the hydrolysis method, and is, in general, about 0 to 300° C., preferably about 10 to 200° C. and more preferably about 50 to 150° C.

In the case of the alkali-hydrolysis, the dicarboxylic acid salt of the formula (3) is formed, and in the case of the acid-hydrolysis, the dicarboxylic acid of the formula (3) is formed. The dicarboxylic acid and the salt thereof can be interconverted each other by a conventional method (a reaction with a base or an acid). For example, to an aqueous solution containing the dicarboxylic acid salt is added an acid to react, so that a free dicarboxylic acid corresponding to the above salt can be formed. The amount of the acid in this case, is about 2 or more equivalents (e.g., about 2 to 10 equivalents), preferably about 2 to 6 equivalents, and more preferably about 2 to 4 equivalents relative to 1 equivalent (1 mol) of the dicarboxylic acid salt.

As the reactive derivative of the dicarboxylic acid, there may be mentioned a derivative obtained by activating a carboxyl group, for example, a mono- or diester, a mono- or diamide, an acid anhydride (a compound represented by the formula (5)), and an acid halide, which correspond to the dicarboxylic acid. Among them, the acid anhydride of the dicarboxylic acid is particularly preferred.

The mono- or diester of the dicarboxylic acid includes, for example, an alkyl ester (in particular, a $C_{1-4}$alkylester) such as methylester, ethylester, isopropyl ester, isobutyl ester, and t-butyl ester; an alkenyl ester (in particular, a $C_{2-4}$alkenyl ester) such as vinyl ester and allyl ester; an aralkyl ester such as benzyl ester; an aryl ester such as phenyl ester. Among them, a mono- or di$C_{1-4}$alkyl ester of the dicarboxylic acid or the like is preferred.

The mono- or diamide of the dicarboxylic acid includes, for example, non-substituted amide, alkyl amide such as methyl amide, ethyl amide and N,N-dimethyl amide; aralkyl amide such as benzyl amide; aryl amide such as anilide. The halide of the dicarboxylic acid includes, for example, acid chloride and acid bromide.

These reactive derivatives of the dicarboxylic acid can be produced by a method which is usually employed in the production of the corresponding reactive derivative from a carboxylic acid in general. For example, the ester of the dicarboxylic acid can be obtained by reacting a dicarboxylic acid with an alcohol corresponding to the desired ester in the presence of an acid catalyst, if necessary, with removing by-produced water. Moreover, the amide of the dicarboxylic acid can be obtained by reacting a dicarboxylic acid with ammonia or an amine corresponding to the desired amide, if necessary in the presence of a condensing agent. Moreover, the dicarboxylic acid can be converted into an acid anhydride of the dicarboxylic acid (a compound represented by the formula (5)) by a suitable dehydrating agent (e.g., sulfuric acid, diphosphorus pentaoxide, thionyl halide, phosgene, phosphoric acid halide, acid halide, acid anhydride, carbodiimide, acylimidazol). Incidentally, in this case, the reaction may be carried out with removing water by-produced. Further, the dicarbocxylic acid can be converted into the corresponding acid halide by action of a thionyl halide such as thionyl chloride, phosphorus, or a halide of the phosphoric acid.

In the process of the present invention, when the dicarboxylic acid or its salt, or a reactive derivative of the dicarboxylic acid is reacted with hydroxylamine, the reaction is usually carried out in the presence of a solvent. As the solvent, there may be mentioned an alcohol such as methanol, ethanol, and isopropanol; an aromatic hydrocarbon such as benzene and toluene; a halogenated hydrocarbon such as carbon tetrachloride, chloroform, dichloromethane, 1,2-dichloroethane; an aliphatic hydrocarbon such as pentane, hexane, heptane and octane; an alicyclic hydrocarbon such as cyclohexane and methylcyclohexane; an ester such as ethyl acetate and butyl acetate; an ether such as diethyl ether, dioxane, tetrahydrofuran; an basic solvent such as pyridine; a nitril such as acetonitrile; a non-protonic polar solvent such as N,N-dimethylformamide and dimethylsulfoxide.

It is preferred for reasons of improving a yield that as the dicarboxylic acid or salt thereof used in the reaction, one isolated in the above step is employed. Moreover, when a reactive derivative (e.g., acid anhydride) of a dicarboxylic acid is employed in the reaction, it is preferred that a reactive derivative isolated or a reactive derivative obtained from a dicarboxylic acid isolated is employed for the same reasons.

As the hydroxylamine, a free hydroxylamine may be employed, or a salt of hydroxylamine may be employed. When the salt of hydroxylamine is employed, a basic solvent such as pyridine is employed, or an appropriate base (an organic base or an inorganic base) is added to the reaction system. Incidentally, when a salt of a dicarboxylic acid is employed as a raw material for reaction, without particularly using a basic material, a salt of hydroxylamine can be employed.

The salt of hydroxylamine includes an inorganic acid salt such as hydrochloride, sulfate, nitrate and phosphate; an organic acid salt such as acetate. As the base, there may be mentioned, for example, an amine such as triethylamine and piperidine; a nitrogen containing heterocyclic compound such as pyridine; an alkali metal alkoxide such as sodium methoxide and sodium ethoxide; an alkali metal salt of an organic acid such as sodium acetate and potassium acetate; ammonia; an alkali metal hydroxide such as sodium hydroxide and potassium hydroxide; an alkali metal carbonate such as sodium carbonate and potassium carbonate; an alkali metal hydrogencarbonate such as sodium hydrogencarbonate and potassium hydrogencarbonate; an alkaline earth metal hydroxide such as magnesium hydroxide and calcium hydroxide.

The amount of hydroxylamine (or a salt thereof) is usually about 1 mol or more (e.g., about 1 to 10 mol), preferably about 1 to 5 mol and more preferably about 1 to 3 mol relative to 1 mol of a treated component such as the dicarboxylic acid. Incidentally, hydroxylamine may be used as a solvent.

The reaction temperature is, in general, about 0 to 150° C., preferably about 5 to 120° C. In order to accelerate reaction, the reaction may be carried out with removing water by-produced, or a scavenger of water (a dehydrating agent) is added to the reaction system.

After completion of reaction, the regenerated imide catalyst can be separated and purified by a conventional separating and purifying means, for example, filtration, condensation, extraction, crystallization, recrystallization. Incidentally, the crystallization or recrystallization is carried out under an acidic condition (e.g., pH of about 2 to 6), so that a high-purity imide catalyst can be obtained with high yield.

When the dicarboxylic acid or its salt, or the reactive derivative of the dicarboxylic acid is treated with an acid after reacting with O-substituted hydroxylamine, an O-organic group-substituted hydroxylamine in which the organic group is attached at oxygen atom such as an O-alkyl-substituted hydroxylamine, an O-cycloalkyl-substituted hydroxylamine, an O-aralkyl-substituted hydroxylamine, and an O-aryl-substituted hydroxylamine can be employed as the O-substituted hydroxylamine.

As the O-alkyl-substituted hydroxylamine, there may be mentioned, for example, an O—$C_{1-4}$alkyl-substituted hydroxylamine such as O-methylhydroxylamine, O-ethylhydroxylamine, O-isopropylhydroxylamine and O-t-butylhydroxylamine. As the O-cycloalkyl-substituted hydroxylamine, there may be mentioned, for example, O-cyclopentylhydroxylamine, and O-cyclohexylhydroxylamine, the O-aralkyl-substituted hydroxylamine includes, for example, O-benzylhydroxylamine, and the O-aryl-substituted hydroxylamine includes O-phenylhydroxylamine.

The reaction can be carried out according to the reaction of the dicarboxylic acid or the like with hydroxylamine. By the reaction, for example, N-substituted oxy cyclic imide compound having a unit represented by the following formula (6) is formed:

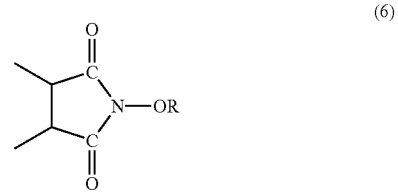

(6)

Wherein R is an organic group.

The organic group of R includes the corresponding organic groups to the O-organic group-substituted hydroxylamines. The typical examples of the group includes, for example, an alkyl group (in particular, a $C_{1-4}$alkyl group) such as methyl, ethyl, isopropyl, and t-butyl groups; a cycloalkyl group such as cyclopentyl and cyclohexyl groups; an aralkyl group such as benzyl group; an aryl group such as phenyl group.

The imide compound of the formula (1) can be regenerated by treating the N-substituted oxy cyclic imide compound obtained thereby with an acid.

The treatment with an acid is usually carried out in the presence of a solvent. As the solvent, the above-exemplified one can be employed. As an acid, there may be mentioned an inorganic acid such as hydrogen fluoride, hydrogen chloride, hydrogen bromide, hydrofluoric acid, hydrochloric acid, hydrobromic acid, sulfuric acid, nitric acid, and phosphoric acid; a sulfonic acid such as methanesulfonic acid, ethanesulfonic acid, benzenesulfonic acid and p-toluenesulfonic acid. It is preferred that the acid is anhydride. The amount of the acid is usually about 1 to 5 mol, preferably about 1 to 3 mol, more preferably about 1 to 2 mol relative to 1 mol of N-substituted oxy cyclic imide compound. The acid may be employed as a solvent.

The treatment temperature with an acid is, for example, about 0 to 100° C., preferably about 5 to 50° C. After treating with an acid, the regenerated imide catalyst can be separated and purified by a conventional separating and purifying means in similar manner to the above.

The imide catalyst regenerated by the process of the present invention can be recycled and reused to the reaction system.

[Process for Regenerating the Imide Compound]

The regenerating process comprises:

a reaction step for reacting the substrate in the presence of the imide compound of the formula (1), a separation step for separating a reaction product formed in the reaction step and the catalyst (including an deactivated catalyst), a catalyst-regeneration step for regenerating the imide compound by hydrolyzing the deactivated catalyst in the reaction step to convert into the dicarboxylic acid of the formula (3) or its salt, then reacting the dicarboxylic acid or its salt, or a reactive derivative of the dicarboxylic acid with (i) hydroxylamine or (ii) O-substituted hydroxylamine, and treating with an acid, and a recycling step for recycling the imide catalyst regenerated to the reaction step.

FIG. 1 is a schematic flow chart illustrating an example of the production process of the present invention.

In the reaction step, the substrate supplied from a line 1 is subjected to reaction in the presence of the imide compound. As the imide compound, an only catalyst regenerated in the regeneration step may be used or the regenerated catalyst may be used in combination with unused new catalyst. The regenerated catalyst is recycled from a line 5. As the species of the reaction, there may be mentioned the above exemplified reaction, for example, an oxidation reaction, a carboxylation reaction, a nitration reaction, a sulfonation reaction, an acylation reaction, a radical-coupling reaction. An reaction apparatus used in the reaction step may comprise, for example, a reactor for reacting the organic substrate, a supply means for supplying the reactive component and the catalyst to the reactor (e.g., a charging line, a charging pump), a mixing means for mixing the reactive component and the catalyst (e.g., stirrer), and if necessary, a reaction temperature-controlling means for controlling a reaction temperature, an exhaust means for exhausting the reaction mixture from the reactor.

In the separating step, the reaction product and the catalyst (including the deactivated catalyst) are separated from the reaction mixture supplied from the reaction step via a line 2. The separation of the reaction product and the catalyst can be carried out by the above separating method (A) (B) or a conventional separating method and a conventional separating apparatus (e.g., a filtration apparatus, a condensation apparatus, a distillation apparatus, an extraction apparatus, an adsorption apparatus, a column chromatography). The reaction product separated is recovered though a line 4, and if necessary further purifying. Part or all of the separated catalysts are subjected to the regeneration step via a line 3 to be regenerated. Incidentally, when part of the catalyst used in the reaction is subjected to the regeneration step, the residual catalyst can be recycled to the reaction step without regeneration.

In the regeneration step, the deactivated catalyst supplied via the line 3 from the separating step is regenerated according to the regeneration process of the imide compound. An apparatus for regenerating the deactivated catalyst can comprise, for example, a reactor for reacting a reactive component such as the deactivated catalyst, a supply means for supplying the reactive component (e.g., a charging line, a charging pump) to the reactor, a mixing means for mixing the reactive component (e.g., stirrer), and if necessary a reaction temperature-controlling means for controlling a reaction temperature, a pH-controlling means for controlling pH of the reaction system, an exhaust means for exhausting the reaction mixture from the reactor, a separation and purification means for separating and purifying the regenerated catalyst and the like.

In the recycle step, the regenerated catalyst recovered from the regeneration step via the line 5 is recycled to the reaction step. The recycle of the regenerated catalyst can be carried out by a conventional method such as supplying the regenerated catalyst to the reaction system, e.g., without any treatment, or with dissolving or suspending in an appropriate solvent. For example, as the recycle means, a pump, a beltconver or the like can be used. Incidentally, the operation in each step may be carried out whichever a continuous manner or a batch manner. Moreover, a single or a plurality of apparatuses such as a reactor or equipments in each step can be used.

INDUSTRIAL APPLICABILITY OF THE INVENTION

According to the present invention, from a reaction mixture obtained by reacting a substrate in the presence of the imide compound, the imide compound and the reaction product can be efficiently separated. Further, from the reaction mixture, the imide compound and the metal catalyst can be also separated efficiently. Furthermore, according to the present invention, among the imide compound separated, the imide compound deactivated by the reaction can be efficiently regenerated.

EXAMPLES

The following examples are intended to describe the present invention in more detail, but should by no means be construed to limit the scope of the invention.

Example A1-1

To an autoclave (volume 1 L) made of titanium and equipped with a condenser and a pressure-controller, were added 50 g (0.594 mol) of cyclohexane, 9.692 g (0.059 mol) of N-hydroxyphthalimide, 0.296 g (0.0012 mol) of cobalt acetate (II) tetrahydrate and 400 g of acetonitrile, and heated to elevate a temperature under applied nitrogen-pressure (33 kgf/cm$^2$; 3.24 MPa) with stirring. At a temperature of 75° C. was steadied, and a reaction was conducted for 4 hours under applied pressure (40 kgf/cm$^2$; 3.92 MPa) with flowing air. The system was substituted with nitrogen to be cooled.

The reaction mixture was analyzed by gas chromatography and high performance liquid chromatography, and, as a result, the conversion of cyclohexane was 19.5%, cyclohexanone and cyclohexanol were formed in yield 14.5% (selectivity 74.4%) and yield 1.6% (selectivity 8.2%), respectively. Moreover, in the reaction mixture, 9.080 g of N-hydroxyphthalimide used as a catalyst, 0.109 g of phthalimide which was deactivated product of N-hydroxyphthalimide, 0.138 g of phthalic anhydride which was also deactivated product of N-hydroxyphthalimide existed.

After the reaction mixture was filtrated to remove an insoluble material, the filtrate was condensed to distill off cyclohexane and acetonitrile. To the condensed residue was added 100 mL of cyclohexane, stirred for 1 hour, and then filtrated to recover the catalyst and the decomposed product thereof (N-hydroxyphthalimide, phthalimide and phthalic anhydride) in the form of solid. The filtrate did not contain the catalyst and the decomposed product thereof.

Example A1-2

A mixture of 25 g (164 mmol) of adamantanol, 5.36 g (32.8 mmol) of N-hydroxyphthalimide, 0.11 g (0.328 mmol) of vanadiumacetylacetonato [V(acac)$_3$], 150 mL of acetic acid and 150 mL of chlorobenzene was stirred for 20 hours at 85° C. and 1 atm (0.101 MPa) in an atmosphere of oxygen. After completion of reaction, the reaction mixture was analyzed by gas chromatography and high performance liquid chromatography, and, as a result, the conversion of adamantanol was 95.6%, adamantanediol and adamantanetriol were formed in yield 50.5% (selectivity 52.8%) and yield 40.7% (selectivity 42.6%), respectively. Moreover, in the reaction mixture, 1.85 g of N-hydroxyphthalimide used as a catalyst, 1.51 g of phthalimide, and 0.40 g of phthalic anhydride were contained.

The reaction mixture was condensed, 1.2 L of water was added thereto, and the mixture was stirred for 2 hours at 50° C. After cooling, an insoluble material was filtrated to recover the catalyst and the decomposed product thereof in the form of solid. The filtrate was extracted three times with 3 L of ethyl acetate. The extract liquid was condensed to 170 g, the resulting crystalline was filtrated to obtain 11.2 g of adamantanediol. The crystalline did not contain the catalyst and the decomposed product thereof. Moreover, the residual extract liquid was condensed to 100 g and 200 g of acetone was added thereto. The resulting crystalline was filtrated to obtain 9.9 g of adamantanetriol. The crystalline did not contain the catalyst and the decomposed product thereof.

Example A1-3

A mixture of 27 g (200 mmol) of adamantane, 3.25 g (20 mmol) of N-hydroxyphthalimide, 0.183 g (0.1 mmol) of V$_2$O$_5$, 240 mL of anisol and 60 mL of acetic acid was stirred for 3 hours at 85° C. and 1 atm (0.101 MPa) in an atmosphere of oxygen. After completion of reaction, the reaction mixture was analyzed by gas chromatography and high performance liquid chromatography, and, as a result, the conversion of adamantane was 13.0%, adamantanol and adamantanone were formed in yield 11.3% (selectivity 86.9%) and yield 0.9% (selectivity 6.9%), respectively. Moreover, in the reaction mixture, 2.12 g of N-hydroxyphthalimide used as a catalyst, 0.68 g of phthalimide, and 0.18 g of phthalic anhydride were contained. The reaction mixture was condensed, 400 mL of hexane was added thereto, and the mixture was stirred for 2 hours at 50° C. After cooling, an insoluble material was filtrated to recover the catalyst and the decomposed product thereof in the form of solid. The filtrate did not contain the catalyst and the decomposed product thereof.

Example A2-1

To a reactor were added p-xylene, N-hydroxyphthalimide (NHPI), cobalt acetate, manganese acetate and acetic acid, and reaction was conducted at 150° C. and 4 MPa in an atmosphere of 50% of oxygen (balance: N$_2$) to obtain a reaction mixture. The composition of the oxidation reaction mixture was 20 g of terephthalic acid, 190 g of acetic acid, 0.2 g of NHPI, 2.0 g of phthalic acid (PA), 2.5 g of phthalimide (PI), 0.3 g of phthalic anhydride (APA), 0.3 g of p-xylene, 0.4 g of 4-carboxybaenzaldehyde (4-CBA), 0.8 g of p-toluic acid (p-TA), 0.1 g of cobalt acetate and 0.1 g of manganese acetate.

The reaction mixture was cooled to 80° C. at atmospheric pressure, a crystalline was filtrated at 80° C. and 300 mmHg, and the residue washed with 60 g of acetic acid under the same condition.

In the resulting crystalline, the distribution ratio of terephthalic acid was 99.7%, and NHPI and the deactivated thereof were not detected. Incidentally, the distribution ratio means a ratio (weight basis) of the content of terephthalic acid in a crystalline relative to the content of terephthalic acid in an oxidation reaction mixture.

Example A2-2

To a reactor were added p-xylene, N-acetoxyphthalimide (NAPI), cobalt acetate, manganese acetate and acetic acid, and reaction was conducted at 150° C. and 4 MPa in an atmosphere of 50% of oxygen (balance: N$_2$) to obtain a reaction mixture. The composition of the oxidation reaction mixture was 20 g of terephthalic acid, 190 g of acetic acid, 0.1 g of NAPI, 0.2 g of NHPI, 2.0 g of phthalic acid (PA), 2.5 g of phthalimide (PI), 0.2 g of phthalic anhydride (APA), 0.3 g of p-xylene, 0.4 g of 4-carboxybaenzaldehyde (4-CBA), 0.8 g of p-toluic acid (p-TA), 0.1 g of cobalt acetate and 0.1 g of manganese acetate.

The reaction mixture was cooled to 80° C. at atmospheric pressure, a crystalline was filtrated at 80° C. and 300 mmHg, and the residue washed with 60 g of acetic acid under the same condition.

In the resulting crystalline, the distribution ratio of terephthalic acid was 99.8%, and NAPI and the deactivated thereof were not detected.

Example A2-3

To a reactor were added m-xylene, N-hydroxyphthalimide (NHPI), cobalt acetate, manganese acetate and acetic acid, and reaction was conducted at 150° C. and 4 MPa in an atmosphere of 50% of oxygen (balance: N$_2$) to obtain a reaction mixture. The composition of the oxidation reaction mixture was 20 g of isophthalic acid, 190 g of acetic acid, 0.2 g of NHPI, 2.0 g of phthalic acid (PA), 2.5 g of phthalimide (PI), 0.3 g of phthalic anhydride (APA), 0.3 g of m-xylene, 0.4 g of 3-carboxybaenzaldehyde (3-CBA), 0.8 g of m-toluic acid (m-TA), 0.1 g of cobalt acetate and 0.1 g of manganese acetate.

The reaction mixture was cooled to 80° C. at atmospheric pressure, a crystalline was filtrated at 80° C. and 300 mmHg, and the residue washed with 60 g of acetic acid under the same condition.

In the resulting crystalline, the distribution ratio of isophthalic acid was 98.5%, and NHPI and the deactivated thereof were not detected.

Example A2-4

To a reactor were added m-xylene, N-acetoxyphthalimide (NAPI), cobalt acetate, manganese acetate and acetic acid, and reaction was conducted at 150° C. and 4 MPa in an atmosphere of 50% of oxygen (balance: N$_2$) to obtain a reaction mixture. The composition of the oxidation reaction mixture was 20 g of isophthalic acid, 190 g of acetic acid, 0.1 g of NAPI, 0.2 g of NHPI, 2.0 g of phthalic acid (PA), 2.5 g of phthalimide (PI), 0.2 g of phthalic anhydride (APA), 0.3 g of m-xylene, 0.4 g of 3-carboxybaenzaldehyde (3-CBA), 0.8 g of m-toluic acid (m-TA), 0.1 g of cobalt acetate and 0.1 g of manganese acetate.

The reaction mixture was cooled to 80° C. at atmospheric pressure, a crystalline was filtrated at 80° C. and 300 mmHg, and the residue washed with 60 g of acetic acid under the same condition.

In the resulting crystalline, the distribution ratio of isophthalic acid was 98.7%, and NAPI and the deactivated thereof were not detected.

Example A2-5

To a reactor were added β-picoline, N-hydroxyphthalimide (NHPI), nicotinaldehyde, cobalt acetate, manganese acetate and acetic acid, and reaction was conducted at 100° C. and 4 MPa in an atmosphere of air to obtain a reaction mixture. The composition of the oxidation reaction mixture was 26 g of nicotinic acid, 233 g of acetic acid, 0.1 g of NHPI, 3.0 g of phthalic acid (PA), 1.5 g of phthalimide (PI), 0.1 g of phthalic anhydride (APA), 43 g of β-picoline, 0.5 g of nicotinaldehyde, 3.3 g of water, 0.5 g of cobalt acetate and 0.5 g of manganese acetate.

The reaction mixture was condensed at 60 to 70° C. and 80 mmHg, and the condensate was cooled to 25° C. at atmospheric pressure. A crystalline was filtrated at 25° C. and 200 mmHg, and the residue washed with 27 g of acetic acid under the same condition.

In the resulting crystalline, the distribution ratio of nicotinic acid was 98%, and NHPI and the deactivated thereof were not detected.

Example A2-6

To a reactor were added β-picoline, N-acetoxyphthalimide (NAPI), nicotinaldehyde, cobalt acetate, manganese acetate and acetic acid, and reaction was conducted at 140° C. and 2 MPa in an atmosphere of air to obtain a reaction mixture. The composition of the oxidation reaction mixture was 20 g of nicotinic acid, 307 g of acetic acid, 0.05 g of NAPI, 0.1 g of NHPI, 3.0 g of phthalic acid (PA), 1.8 g of phthalimide (PI), 0.7 g of phthalic anhydride (APA), 20 g of β-picoline, 0.2 g of nicotinaldehyde, 5.5 g of water, 0.3 g of cobalt acetate and 0.3 g of manganese acetate.

The reaction mixture was condensed at 60 to 80° C. and 80 mmHg. To the condensate was added 62 g of 2-ethylhexanol and cooled to 25° C. at atmospheric pressure. A crystalline was filtrated at 25° C. and 200 mmHg, and the residue washed with 68 g of methanol under the same condition.

In the resulting crystalline, the distribution ratio of nicotinic acid was 91%, and NAPI and the deactivated thereof were not detected.

Example A2-7

To a reactor were added 1,2,4,5-tetramethylbenzene, N-acetoxyphthalimide (NAPI), cobalt acetate, manganese acetate and acetic acid, and reaction was conducted at 150° C. and 5 MPa in an atmosphere of 60% of oxygen (balance: $N_2$) to obtain a reaction mixture. The composition of the oxidation reaction mixture was 3.3 g of pyromellitic acid, 65 g of acetic acid, 0.01 g of NAPI, 0.1 g of NHPI, 0.3 g of phthalic acid (PA), 0.3 g of phthalimide (PI), 0.1 g of phthalic anhydride (APA), 1.6 g of water, 0.03 g of cobalt acetate and 0.06 g of manganese acetate.

The reaction mixture was cooled to 50° C. at atmospheric pressure, a crystalline was filtrated at 50° C. and 200 mmHg, and the residue washed with 27 g of acetic acid under the same condition.

In the resulting crystalline, the distribution ratio of pyromellitic acid was 99%, and the deactivated thereof was not detected.

Example A2-8

To a reactor were added p-t-butyltoluene, N-hydroxyphthalimide (NHPI), cobalt acetate and acetic acid, and reaction was conducted at 80° C. and 2 MPa in an atmosphere of air to obtain a reaction mixture. The composition of the oxidation reaction mixture was 112.1 g of t-butylbenzoic acid, 16.8 g of t-butylbenzaldehyde, 271.2 g of acetic acid, 0.9 g of NHPI, 0.2 g of phthalic acid (PA), 2.7 g of phthalimide (PI), and 0.1 g of cobalt acetate.

The reaction mixture was supplied to a distillation column (column plates: 10, reflux ratio: 5, pressure: 120 mmHg) and condensed. The condensate was cooled to 2° C. at atmospheric pressure, a crystalline was filtrated, and the residue washed with 50% by weight of acetic acid aqueous solution (671 g) under the same condition.

In the resulting crystalline, the distribution ratio of t-butylbenzoic acid was 96%, and NHPI and the deactivated thereof were not detected.

Example A2-9

To a reactor were added cyclohexane, N-hydroxyphthalimide (NHPI), cobalt acetate, cobaltacetylacetonato and acetic acid, and reaction was conducted at 120° C. and 2 MPa in an atmosphere of oxygen gas to obtain a reaction mixture. The composition of the oxidation reaction mixture was 32.1 g of adipic acid, 6.0 g of glutaric acid, 4.1 g of succinic acid, 164.6 g of acetic acid, 0.04 g of NHPI, 0.3 g of phthalic acid (PA), 0.2 g of phthalimide (PI), 68.8 g of cyclohexane, 8.2 g of water, 0.1 g of cobalt acetate and 0.8 g of cobaltacetylacetonato.

The reaction mixture was cooled to 30° C. at atmospheric pressure, and a crystalline was filtrated at 30° C. and 200 mmHg.

Further, to the residue was added 25.9 g of water, dissolved completely, and cooled to 30° C. at atmospheric pressure to obtain a crystalline. The crystalline was filtrated at 30° C. and 200 mmHg.

In the resulting crystalline, the distribution ratio of adipic acid was 60%, and NHPI and the deactivated thereof were not detected.

Example B1

To an oxidation reaction mixture containing 33 g (0.22 mol) of p-t-butyltoluene, 4.3 g (24.3 mmol) of p-t-butylbenzoic acid, 2.8 g (17.5 mmol) of p-t-butylbenzaldehyde, 0.2 g (1.77 mmol) of N-hydroxymaleimide, 0.15 g (1.54 mmol) of maleimide, and 0.1 g (1.02 mmol) of maleic anhydride, was added water (30 mL), and mixed completely, and allowed to stand to liquid-separate. Further, to the organic phase was added to water (30 mL) and mixed completely to liquid-separate. The resulting aqueous and organic phases were analyzed by gas chromatography and liquid chromatography, and, as a result, the recover ratio of p-t-butylbenzoic acid into the organic phase was 93%, the extraction ratio of p-t-butylbenzaldehyde into the organic phase was 87%, the recover ratio of N-hydroxymaleimide into the aqueous phase was 82%, the extraction ratio of maleimide into the aqueous phase was 68%, and the extraction ratio of maleic anhydride into the aqueous phase was 95%.

Example B2

A mixture containing 3 kg (20.2 mol) of p-t-butyltoluene, 66.03 g (0.405 mol) of N-hydroxyphthalimide, 2.5 kg of acetic acid was allowed to react at 80° C. and 20 kgf/cm² (1.96 MPa) in an atmosphere of oxygen for 2.5 hours to obtain a reaction mixture containing 50.8 g (0.309 mol) of p-t-butylbenzylalcohol, 206.8 g (1.275 mol) of p-t-butylbenzaldehyde, 1121.9 g (6.295 mol) of p-t-butylbenzoic acid, 12.2 g (0.075 mol) of N-hydroxyphthalimide, 22.0 g (0.150 mol) of phthalimide and 8.5 g (0.057 mol) of phthalic anhydride. To this reaction mixture was added 2600 mL of water, mixed completely for 1 hour, and then allowed to stand for 1 hour to liquid-separate into an aqueous phase and an organic phase. The resulting aqueous and organic phases were analyzed by gas chromatography and liquid chromatography, and, as a result, the recover ratio of p-t-butylbenzylalcohol into the organic phase was 75%, the recover ratio of p-t-butylbenzaldehyde into the organic phase was 97%, the recover ratio of p-t-butylbenzoic acid into the organic phase was 96%. Moreover, the extraction ratio of N-hydroxyphthalimide (on basis of the amount of N-hydroxyphthalimide contained in the reaction mixture) into the aqueous phase was 80%, the extraction ratio (on basis of the amount of phthalimide contained in the reaction mixture) of phthalimide into the aqueous phase was 90%, and the extraction ratio of phthalic anhydride (on basis of the amount of phthalic anhydride contained in the reaction mixture) into the aqueous phase was 59%.

Example B3

A mixture containing 166 g (1 mol) of fluorene, 16 g (0.1 mol) of N-hydroxyphthalimide, and 1000 mL of acetic acid was allowed to react at 100° C. for 10 hours in an atmosphere of oxygen to obtain a reaction mixture containing 144 g of fluorenone (yield 80%). From the reaction mixture, acetic acid was distilled off, and to the reaction mixture were added 1000 mL of dibutyl ether and 1000 mL of 0.4N (0.4 mol/L) sodium hydroxide aqueous solution. After stirring at 97° C. for 1 hour, an aqueous phase and an organic phase were separated. To the resulting organic phase were further added sodium hydroxide aqueous solution, and mixed completely at 97° C. to liquid-separate to the aqueous phase and the organic phase. The resulting aqueous and organic phases were analyzed by gas chromatography and liquid chromatography, and, as a result, the extraction ratio of fluorenone into the organic phase was 98%, the extraction ratio of the oxidation catalyst and/or the deactivated oxidation catalyst (conversion into sodium phthalate) (on basis of the amount of N-hydroxyphthalimide used in the reaction) into the aqueous phase was 80%.

Example B4

A mixture containing 168 g (1 mol) of diphenylmethane, 16 g (0.1 mol) of N-hydroxyphthalimide, and 1000 mL of acetic acid was allowed to react at 100° C. for 20 hours in an atmosphere of oxygen to obtain a reaction mixture containing 146 g of benzophenone (yield 80%). From the reaction mixture, acetic acid was distilled off, and to the reaction mixture were added 1000 mL of dibutyl ether and 1000 mL of 0.4N sodium hydroxide aqueous solution. After stirring at 97° C. for 1 hour, an aqueous phase and an organic phase were separated. To the resulting organic phase was further added sodium hydroxide aqueous solution, and mixed completely at 97° C. to liquid-separate into an aqueous phase and an organic phase. The aqueous and organic phases were analyzed by gas chromatography and liquid chromatography, and, as a result, the extraction ratio of benzophenone into the organic phase was 89%, the extraction ratio of the oxidation catalyst and/or the deactivated oxidation catalyst (conversion into sodium phthalate) (on basis of the amount of N-hydroxyphthalimide used in the reaction) into the aqueous phase was 83%.

Example B5

A mixture containing 1500 g (17.82 mol) of cyclohexane, 3.16 g (0.019 mol) of N-hydroxyphthalimide, and 0.045 g (0.18 mol) of cobalt acetate was allowed to react at 160° C. and 40 kgf/cm² (3.92 MPa) for 2 hours in an atmosphere of oxygen to obtain a reaction mixture containing 1334 g (15.84 mol) of cyclohexane, 83.89 g (0.84 mol) of cyclohexanol, 59.47 g (0.61 mol) of cyclohexanone, 1.77 g (0.012 mmol) of phthalimide and 1.30 g (0.005 mol) of N-cyclohexyloxyphthalimide. From the reaction mixture, cyclohexane was distilled off, and to the reaction mixture was added 30 mL of 2N (2 mol/L) sodium hydroxide aqueous solution. After mixing at 97° C. for 1 hour completely and standing for 1 hour, an aqueous phase and an organic phase were separated. The aqueous and organic phases were analyzed by gas chromatography and liquid chromatography, and, as a result, the recover ratio of cyclohexanol into the organic phase was 85%, the recover ratio of cyclohexanone into the organic phase was 90%, the extraction ratio of phthalimide (conversion into sodium phthalate) into the aqueous phase (on basis of the amount of phthalimide in the reaction mixture) was 89% and the extraction ratio of N-cyclohexyloxyphthalimide (conversion into sodium phthalate) into the aqueous phase (on basis of the amount of N-cyclohexylphthalimide) was 90%.

Example B6

A mixture containing 300 g (2.02 mol) of p-t-butyltoluene, 6.60 g (0.04 mol) of N-hydroxyphthalimide, 0.10 g (0.0004 mol) of cobalt acetate and 293.3 g (4.88 mol) of acetic acid was allowed to react at 80° C. and 20 kgf/cm² (1.96 MPa) for 3 hours in an atmosphere of oxygen to obtain a reaction mixture containing 162.5 g (1.09 mol) of p-t-butyltoluene, 106.2 g (0.59 mol) of p-t-butylbenzoic acid, 17.7 g (0.11 mol) of p-t-butylbenzaldehyde, 0.26 g (1.62 mmol) of N-hydroxyphthalimide, 3.98 g (27.1 mmol) of phthalimide. Acetic acid was distilled off from the reaction mixture with a condensation apparatus, and the deposited p-t-butylbenzoic acid was recovered by filtration. To the filtrate was added 150 mL of 0.1N (0.1 mol/L) sodium hydroxide aqueous solution, mixed completely, and allowed to stand to liquid-separate. The aqueous and organic phases were analyzed by gas chromatography and liquid chromatography, and, as a result, the recover ratio of p-t-butylbenzaldehyde into the organic phase was 91%, the extraction ratio of N-hydroxyphthalimide (conversion into sodium salt of N-hydroxyphthalimide) (on basis of the amount of N-hydroxyphthalimide in the reaction mixture) into the aqueous phase was 97%, the extraction ratio of phthalimide (conversion into sodium phthalate) (on basis of the amount of phthalimide in the reaction mixture) into the aqueous phase was 93%.

Example C1

In the presence of an oxidation catalyst (N-acetoxyphthalimide (NAPI)) and a metal catalyst (cobalt acetate and manganese acetate), p-xylene was oxidized in acetic acid solvent at 150° C. and 4 MPa with 50% of oxygen (balance: nitrogen) air to produce terephthalic acid. The reaction mixture was cooling-crystallized to 80° C. at atmospheric pressure and filtrated, and the residue was washed with acetic acid and filtrated to separate terephthalic acid. The filtrate and washing liquid were combined and acetic acid was removed therefrom. The components in the condensed residue were analyzed, and as a result, 2.7 g of terephthalic acid, 7.8 g of acetic acid, 0.2 g of N-acetoxyphthalimide (NAPI), 0.2 g of N-hydroxyphthalimide (NHPI), 1.2 g of phthalic acid (PA), 1.4 g of phthalimide (PI), 0.4 g of phthalic anhydride (APA), 0.3 g of p-xylene, 7.8 g of 4-carboxybenzaldehyde (4-CBA), 22.3 g of p-toluic acid (p-TA), 0.4 g of total cobalt, 1.0 g of total manganese were contained.

To the condensate was added 51 g of water, the precipitate was filtrated at 30° C. and 300 mmHg, and to the residue was added 61 g of water and washed under the same condition. The distribution ratio of the total cobalt into the filtrate was 98.4%, the distribution ratio of the total manganese to the filtrate was 98.4%, the distribution ratios to the filtration residue of NAPI, NHPI, PA and PI were 99.2%, 99.1%, 77% and 85%, respectively. Incidentally, the distribution ratio means to a ratio (weight basis) of a component content in the filtrate or the filtration residue relative to a component content in the condensate.

Example C2

In the presence of an oxidation catalyst (N-hydroxyphthalimide (NHPI)) and a metal catalyst (cobalt acetate and manganese acetate), p-xylene was oxidized in acetic acid solvent at 150° C. and 4 MPa with 50% of oxygen (balance: nitrogen) to produce terephthalic acid. The reaction mixture was cooling-crystallized to 80° C. at atmospheric pressure and filtrated, and the residue was washed with acetic acid and filtrated to separate terephthalic acid. The filtrate and washing liquid were combined and acetic acid was removed therefrom. The components in the condensed residue were analyzed, and as a result, 2.7 g of terephthalic acid, 7.7 g of acetic acid, 0.35 g of N-hydroxyphthalimide (NHPI), 1.2 g of phthalic acid (PA), 1.4 g of phthalimide (PI), 0.35 g of phthalic anhydride (APA), 0.3 g of p-xylene, 7.8 g of 4-carboxybenzaldehyde (4-CBA), 22.3 g of p-toluic acid (p-TA), 0.4 g of total cobalt, 1.0 g of total manganese were contained.

To the condensate was added 51 g of water, the precipitate was filtrated at 25° C. and 300 mmHg, and to the residue was added 80 g of water and washed under the same condition. The distribution ratio of the total cobalt into the filtrate was 95.2%, the distribution ratio of the total manganese into the filtrate was 99.5%, the distribution ratios to the filtration residue of NHPI, PA and PI were 99.4%, 70%, and 80%, respectively.

Example C3

In the presence of an oxidation catalyst (N-hydroxyphthalimide. (NHPI)) and a metal catalyst (cobalt acetate and manganese acetate), m-xylene was oxidized in acetic acid solvent at 150° C. and 4 MPa with 50% of oxygen (balance: nitrogen) to produce isophthalic acid. The reaction mixture was cooling-crystallized to 80° C. at atmospheric pressure and filtrated, and the residue was washed with acetic acid and filtrated to separate isophthalic acid. The filtrate and washing liquid were combined and acetic acid was removed therefrom. The components in the condensed residue were analyzed, and as a result, 2.7 g of isophthalic acid, 7.8 g of acetic acid, 0.35 g of N-hydroxyphthalimide (NHPI), 1.2 g of phthalic acid (PA), 1.4 g of phthalimide (PI), 0.35 g of phthalic anhydride (APA), 0.3 g of m-xylene, 7.8 g of 3-carboxybenzaldehyde (3-CBA), 22.3 g of m-toluic acid (m-TA), 0.4 g of total cobalt, 1.0 g of total manganese were contained.

To the condensate was added 51 g of water, the precipitate was filtrated at 25° C. and 300 mmHg, and to the residue was added 80 g of water and washed under the same condition. The distribution ratio of the total cobalt into the filtrate was 96.2%, the distribution ratio of the total manganese into the filtrate was 99.2%, the distribution ratios of NHPI, PA and PI to the filtration residue were 98.9%, 65%, and 75%, respectively.

Example C4

In the presence of an oxidation catalyst (N-acetoxyphthalimide (NAPI)) and a metal catalyst (cobalt acetate and manganese acetate), m-xylene was oxidized in acetic acid solvent at 150° C. and 4 MPa with 50% of oxygen (balance: nitrogen) to produce isophthalic acid. The reaction mixture was cooling-crystallized to 80° C. at atmospheric pressure and filtrated, and the residue was washed with acetic acid and filtrated to separate isophthalic acid. The filtrate and washing liquid were combined and acetic acid was removed therefrom. The components in the condensed residue were analyzed, and as a result, 2.7 g of isophthalic acid, 7.8 g of acetic acid, 0.2 g of N-acetoxyphthalimide (NAPI), 0.2 g of N-hydroxyphthalimide (NHPI), 1.2 g of phthalic acid (PA), 1.4 g of phthalimide (PI), 0.4 g of phthalic anhydride (APA), 0.3 g of m-xylene, 7.8 g of 3-carboxybenzaldehyde (3-CBA), 22.3 g of m-toluic acid (m-TA), 0.4 g of total cobalt, 1.0 g of total manganese were contained.

To the condensate was added 51 g of water, the precipitate was filtrated at 30° C. and 300 mmHg, and to the residue was added 61 g of water and washed under the same condition. The distribution ratio of the total cobalt into the filtrate was 98.2%, the distribution ratio of the total manganese into the filtrate was 98.7%, the distribution ratios to the filtration residue of NAPI, NHPI, PA and PI were 99.2%, 98.9%, 72%, and 79%, respectively.

Example C5

In the presence of an oxidation catalyst (N-hydroxyphthalimide (NHPI)) and a metal catalyst (cobalt acetate and manganese acetate) with nicotinaldehyde as a co-oxidizing agent, β-picoline was oxidized in acetic acid solvent at 140° C. and 2 MPa with air to produce nicotinic acid. From the reaction mixture, acetic acid was removed and to a condensate was added 2-ethylhexanol. The mixture was cooling-crystallized to 25° C. at atmospheric pressure and filtrated, and the residue washed with methanol and filtrated to separate nicotinic acid. The filtrate and washing liquid were combined and the solvent was removed therefrom. The components in the condensed residue were analyzed, and as a result, 94 g of nicotinic acid, 164 g of 2-ethylhexanol, 2.8 g of N-hydroxyphthalimide (NHPI), 113 g of phthalic acid (PA), 67.4 g of phthalimide (PI), 26.2 g of phthalic anhydride (APA), 11 g of total cobalt, 11.4 g of total manganese were contained.

To the condensate was added 100 g of water, the precipitate was filtrated at 30° C. and 300 mmHg, and to the residue was added 30 g of water and washed under the same condition. The distribution ratio of the total cobalt into the aqueous phase was 95.5%, the distribution ratio of the total manganese into the aqueous phase was 99.0%, the distribution ratios to the organic phase and the filtration residue of NHPI, phthalic acid (PA) and phthalimide (PI) were 99.4%, 98%, and 97%, respectively.

Example C6

In the presence of an oxidation catalyst (N-acetoxyphthalimide (NAPI)) and a metal catalyst (cobalt acetate and manganese acetate) with nicotinaldehyde as a co-oxidizing agent, β-picoline was oxidized in acetic acid solvent at 140° C. and 2 MPa with air to produce nicotinic acid. From the reaction mixture, acetic acid was removed and to a condensate was added 2-ethylhexanol. The mixture was cooling-crystallized to 25° C. at atmospheric pressure and filtrated, and the residue washed with methanol and filtrated to separate nicotinic acid. The filtrate and washing liquid were combined and the solvent was removed therefrom. The components in the condensed residue were analyzed, and as a result, 92 g of nicotinic acid, 160 g of 2-ethylhexanol, 1.0 g of N-acetoxyphthalimide (NAPI), 1.8 g of N-hydroxyphthalimide (NHPI), 108 g of phthalic acid (PA), 67 g of phthalimide (PI), 24 g of phthalic anhydride (APA), 11 g of total cobalt, 11.4 g of total manganese were contained.

To the condensate was added 100 g of water, the precipitate was filtrated at 30° C. and 300 mmHg, and to the residue was added 30 g of water and washed under the same condition. The distribution ratio of the total cobalt into the aqueous phase was 98.4%, the distribution ratio of the total manganese to the aqueous phase was 98.2%, the distribution ratios to the organic phase and the filtration residue of NAPI, NHPI, phthalic acid (PA) and phthalimide (PI) were 99.4%, 99.2%, 98% and 99%, respectively.

Example D1

In the presence of an oxidation catalyst (N-hydroxyphthalimide (NHPI)) and a metal catalyst (cobalt acetate and manganese acetate), p-xylene was oxidized in acetic acid solvent at 150° C. and 4 MPa with 50% of oxygen (balance: nitrogen) to produce terephthalic acid. The reaction mixture was cooling-crystallized to 80° C. at atmospheric pressure and filtrated, and the residue was washed with acetic acid and filtrated to separate terephthalic acid. The components in the mixture obtained by combining the filtrate and washing liquid were analyzed, and as a result, 0.14 g of terephthalic acid, 82.7 g of acetic acid, 1.49 g of water ($H_2O$), 0.02 g of N-hydroxyphthalimide (NHPI), 0.06 g of phthalic acid (PA), 0.07 g of phthalimide (PI), 0.01 g of phthalic anhydride (APA), 0.2 g of p-xylene, 0.4 g of 4-carboxybenzaldehyde (4-CBA), 1.14 g of p-toluic acid (p-TA), 0.09 g of total cobalt, 0.23 g of total manganese were contained.

To the mixture was added 4.3 g of a cation exchange resin (manufactured by Mitsubishi Chemical Industries Limited, trade name: strong acidic cation exchange resin "DIAION PK208 porous-type"), and adsorbent treatment was carried out at 25° C. for 3 hours. The distribution ratio of the total cobalt into the ion exchange resin was 96%, the distribution ratio of the total manganese into the ion exchange resin was 92%, and the distribution ratios of NHPI, PA and PI into the mixture treated were 98%, 97% and 98%, respectively. Incidentally, the distribution ratio means to the ratio (weight basis) of the component content adsorbing in the ion exchange resin or the component content in the liquid relative to the component content in the mixture.

Example D2

In the presence of an oxidation catalyst (N-acetoxyphthalimide (NAPI)) and a metal catalyst (cobalt acetate and manganese acetate), p-xylene was oxidized in acetic acid solvent at 150° C. and 4 MPa with 50% of oxygen (balance: nitrogen) to produce terephthalic acid. The reaction mixture was cooling-crystallized to 80° C. at atmospheric pressure and filtrated, and the residue was washed with acetic acid and filtrated to separate terephthalic acid. The components in the mixture obtained by combining the filtrate and washing liquid were analyzed, and as a result, 0.14 g of terephthalic acid, 82.7 g of acetic acid, 1.49 g of water ($H_2O$), 0.01 g of N-acetoxyphthalimide (NAPI), 0.01 g of N-hydroxyphthalimide (NHPI), 0.06 g of phthalic acid (PA), 0.07 g of phthalimide (PI), 0.01 g of phthalic anhydride (APA), 0.1 g of p-xylene, 0.4 g of 4-carboxybenzaldehyde (4-CBA), 1.14 g of p-toluic acid (p-TA), 0.09 g of total cobalt, 0.23 g of total manganese were contained.

To the mixture was added 4.3 g of an anion exchange resin (manufactured by Mitsubishi Chemical Industries Limited, trade name: strong acidic anion exchange resin "SA10A(I-type) gel-type"), and adsorbent treatment was carried out at 30° C. for 3 hours. The distribution ratio of the total cobalt into the ion exchange resin was 72%, the distribution ratio of the total manganese into the ion exchange resin was 65%, and the distribution ratios of NHPI, PA and PI into the mixture treated were 99%, 97% and 95%, respectively.

Example D3

In the presence of an oxidation catalyst (N-hydroxyphthalimide (NHPI)) and a metal catalyst (cobalt acetate and manganese acetate), m-xylene was oxidized in acetic acid solvent at 150° C. and 4 MPa with 50% of oxygen (balance: nitrogen) to produce isophthalic acid. The reaction mixture was cooling-crystallized to 80° C. at atmospheric pressure and filtrated, and the residue was washed with acetic acid and filtrated to separate isophthalic acid. The components in the mixture obtained by combining the filtrate and washing liquid were analyzed, and as a result, 0.14 g of isophthalic acid, 82.7 g of acetic acid, 1.49 g of water ($H_2O$), 0.02 g of N-hydroxyphthalimide (NHPI), 0.06 g of phthalic acid (PA), 0.07 g of phthalimide (PI), 0.01 g of phthalic anhydride (APA), 0.2 g of m-xylene, 0.4 g of 3-carboxybenzaldehyde (3-CBA), 1.14 g of m-toluic acid (m-TA), 0.09 g of total cobalt, 0.23 g of total manganese were contained.

To the mixture was added 4.3 g of a cation exchange resin (manufactured by Mitsubishi Chemical Industries Limited, trade name: strong acidic cation exchange resin "DIAION SK18 gel-type"), and adsorbent treatment was carried out at 25° C. for 3 hours. The distribution ratio of the total cobalt into the ion exchange resin was 95%, the distribution ratio of the total manganese into the ion exchange resin was 92%, and the distribution ratios of NHPI, PA and PI into the mixture treated were 99%, 91% and 97%, respectively.

Example D4

In the presence of an oxidation catalyst (N-hydroxyphthalimide (NHPI)) and a metal catalyst (cobalt acetate and manganese acetate) with nicotinaldehyde as a co-oxidizing agent, β-picoline was oxidized in acetic acid solvent at 140° C. and 2 MPa with air to produce nicotinic acid. From the reaction mixture, acetic acid was removed, to the condensate was added 2-ethylhexanol. The mixture was cooling-crystallized to 25° C. at atmospheric pressure and filtrated, and the residue washed with methanol and filtrated to separate nicotinic acid. The components in the mixture obtained by combining the filtrate and washing liquid were analyzed, and as a result, 9.4 g of nicotinic acid, 160 g of 2-ethylhexanol, 32 g of acetic acid, 63 g of β-picoline, 150 g of methanol, 0.5 g of N-hydroxyphthalimide (NHPI), 10 g of phthalic acid (PA), 8 g of phthalimide (PI), 2.5 g of phthalic anhydride (APA), 1.1 g of total cobalt, 1.1 g of total manganese were contained.

To the mixture was added 21.9 g of a cation exchange resin (manufactured by Mitsubishi Chemical Industries Limited, trade name: chelating resin "CR11imidinoacetic acid type"), and adsorbent treatment was carried out at 25° C. for 3 hours. The distribution ratio of the total cobalt into the ion exchange resin was 94%, the distribution ratio of the total manganese into the ion exchange resin was 91%, and the distribution ratios of NHPI, PA and PI into the mixture treated were 99%, 92% and 95%, respectively.

Example D5

In the presence of an oxidation catalyst (N-hydroxyphthalimide (NHPI)) and a metal catalyst (cobalt acetate and cobaltacetylacetonato), cyclohexane was oxidized in acetic acid solvent at 125° C. and 2 MPa with air to produce adipic acid. The reaction mixture was cooling-crystallized to 10° C. at atmospheric pressure and filtrated to separate adipic acid. The components in the lower layer liquid separated were analyzed, and as a result, 9.94 g of cyclohexane, 0.76 g of cyclohexanone, 0.18 g of cyclohexyl acetate, 0.86 g of cyclohexanol, 73.01 g of acetic acid, 0.58 g of succinic acid, 0.69 g of glutaric acid, 3.04 g of adipic acid, 2.60 g of $H_2O$, 0.01 g of NHPI, 0.45 g of PI, 0.66 g of PA, 0.10 g of total cobalt were contained.

To 50 g of the mixture was added 2.5 g of a cation exchange resin (manufactured by Mitsubishi Chemical Industries Limited, trade name: strong acid cation exchange resin "DIAION PK208 porous-type"), and adsorbent treatment was carried out at 25° C. for 3 hours. The distribution ratio of the total cobalt into the ion exchange resin was 97.5%, and the distribution ratio of NHPI into the mixture treated was 98%. Incidentally, the distribution ratio means to a ratio (weight basis) of the component content adsorbing in the ion exchange resin relative to the component content in the mixture liquid.

Example E1

The mixture of 4.028 g (50 mmol) of cyclohexane, 0.816 g (5 mmol) of N-hydroxyphthalimide, 0.015 g (0.025 mmol) of cobalt(II)acetylacetonato and 200 mL of benzonitrile was reacted at 100° C. for 6 hours in an atmosphere of oxygen to obtain a reaction mixture containing 2.946 g (35 mmol) of cyclohexane, 0.981 g (10 mmol) of cyclohexanone, 0.731 g (2 mmol) of adipic acid, N-hydroxyphthalimide, phthalimide, phthalic acid, cobalt(II)acetylacetonato, and benzonitrile. To the reaction mixture were added cyclohexane (20 mL) and water (150 mL) at 26° C., and mixed completely to be liquid-separated into an aqueous layer and an organic layer. To the resulting organic layer was further added water and mixed completely to be liquid-separated into an aqueous layer and an organic layer. The aqueous layer and the organic layer were analyzed by a liquid chromatography, and as a result, the extraction ratio of N-hydroxyphthalimide (on basis of N-hydroxyphthalimide contained in the reaction mixture) into the organic layer was 79%, the extraction ratio of phthalimide into the organic layer was 82%, the extraction ratio of phthalic acid into the organic layer was 65%, and the extraction ratio of cobalt(II)acetylacetonato (on basis of cobalt(II)acetylacetonato contained in the reaction mixture) into the aqueous layer was 95%.

Example E2

The mixture of 25 g (164.2 mmol) of adamantanol, 5.36 g (32.8 mmol) of N-hydroxyphthalimide, 0.114 g (0.328 mmol) of vanadium(III)acetylacetonato, 150 mL of benzonitrile and 150 mL of acetic acid was reacted at 85° C. for 20 hours in an atmosphere of oxygen to obtain a reaction mixture containing 1.41 g (9.2 mmol) of adamantanol, 13.9 g (82.6 mmol) of adamantanediol, 10.5 g (57.5 mmol) of adamantanetriol, N-hydroxyphthalimide, phthalimide, phthalic acid, vanadium(III)acetylacetonato, and benzonitrile. From the reaction mixture, acetic acid was distilled off. To a condensate was added benzonitrile to 300 mL, 300 mL of water was added at 26° C. thereto, and mixed completely to be liquid-separated into an aqueous layer and an organic layer. To the resulting organic layer was further added water and mixed completely to be liquid-separated into an aqueous layer and an organic layer. The aqueous layer and the organic layer were analyzed by a liquid chromatography, and as a result, the extraction ratio of N-hydroxyphthalimide into the organic layer (on basis of N-hydroxyphthalimide contained in the reaction mixture) was 80%, the extraction ratio of phthalimide into the organic layer was 86%, the extraction ratio of phthalic acid into the organic layer was 75%, and the extraction ratio of vanadium(III)acetylacetonato (on basis of vanadium(III)acetylacetonato contained in the reaction mixture) into the aqueous layer was 93%.

Example E3

The mixture of 9.3 g (100 mmol) of 2-methylpyridine, 1.6 g (10 mmol) of N-hydroxyphthalimide, 0.15 g (0.5 mmol) of cobalt(II)acetylacetonato, 250 mL of acetic acid was reacted at 100° C. for 6 hours in an atmosphere of oxygen to obtain 2-pyridinecarboxylic acid (picolinic acid: yield 77%) with 2-methylpyridine conversion of 82%. From the reaction mixture, acetic acid was distilled off. 400 mL of benzonitrile and 400 mL of water were added thereto, shaken sufficiently, and allowed to stand to be separated into two liquid phases. To the resultant organic layer was further added 400 mL of water, shaken sufficiently, and allowed to stand to be separated into two liquid phases. The aqueous layer and the organic layer were analyzed by a liquid chromatography, and as a result, the extraction ratio of N-hydroxyphthalimide (on basis of N-hydroxyphthalimide contained in the reaction mixture) into the organic layer was 83%, the extraction ratio of phthalimide into the organic layer was 85%, the extraction ratio of phthalic acid into the organic layer was 66%, and the extraction ratio of cobalt(II)acetylacetonato (on basis of cobalt(II)acetylacetonato contained in the reaction mixture) into the aqueous layer was 97%.

Example E4

The mixture of 30.68 kg (0.23 kmol) of adamantane, 5.51 kg (0.03 kmol) of N-hydroxyphthalimide, 0.05 kg (0.0001 kmol) of vanadium(III)acetylacetonato, 204.57 kg of acetic acid was reacted at 90° C. for 4.5 hours in an atmosphere of oxygen to obtain a reaction mixture containing 0.28 kg (0.002 kmol) of adamantane, 6.48 kg (0.04 kmol) of adamantanol, 2.95 kg (0.02 kmol) of adamantanone, 10.73 kg (0.06 kmol) of adamantanediol, 2.78 kg (0.02 kmol) of adamantanetriol, 0.88 kg of N-hydroxyphthalimide, 0.22 kg of phthalimide, 0.05 kg of vanadium(III)acetylacetonato, and acetic acid. From the reaction mixture, acetic acid was distilled off, added 110.31 kg of water and stirred at 40° C., and the precipitate was removed by filtration. To the filtrate, the mixture of 71.60 kg of n-butanol and 71.60 kg of n-heptane was added and mixed at 25° C. completely to be separated into an aqueous layer and an organic layer. To the resulting aqueous layer, the mixture of 61.37 kg of n-butanol and 61.37 kg of n-heptane was added and mixed at 25° C. completely to be separated into an aqueous layer and an organic layer. After the operation was repeated again, the aqueous layer and the organic layer were analyzed by a liquid chromatography, and as a result, the extraction ratio of N-hydroxyphthalimide into the organic layer (on basis of N-hydroxyphthalimide contained in filtrate) was 100%, the extraction ratio of phthalimide into the organic layer was 100%, and the extraction ratio of vanadium(III)acetylacetonato into the aqueous layer (on basis of vanadium(III) acetylacetonato contained in the filtrate) was 83%.

Example F1

To a flask was added 50 mL of 3N sodium hydroxide aqueous solution, and powdery phthalimide (8.8 g, 0.06 mol) was slowly added thereto with stirring. Then, the mixture was stirred at 97° C. for 2 hours to obtain an aqueous solution containing sodium salt of phthalic acid. To the aqueous solution was added diluted hydrochloric acid at ordinary temperature to convert into phthalic acid, and phthalic acid was recovered by condensation and filtration. Then, after hydroxylamine hydrochloride $NH_2OH \cdot HCl$ (8.3 g, 0.12 mol) was dissolved in 100 mL of pyridine, the recovered phthalic acid was added thereto, stirred at 50° C. for 1 hour, and further stirred for 3 hours with elevating the temperature to 95° C. to form N-hydroxyphthalimide (7.3 g, yield 75%).

Example F2

To a flask was added 50 mL of 1N hydrochloric acid, and powdery phthalimide (2.9 g, 20 mmol) was slowly added thereto with stirring. Then, the mixture was stirred at 97° C. for 3 hours to obtain an aqueous solution containing phthalic acid. Phthalic acid was recovered by condensing and filtering the aqueous solution. Then, after hydroxylamine hydrochloride $NH_2OH \cdot HCl$ (1.39 g 40 mmol) was dissolved in 100 mL of pyridine, the recovered phthalic acid was added thereto, and stirred at 97° C. for 4 hour to form N-hydroxyphthalimide (2.3 g yield 71%).

Example F3

To a flask was added 50 mL of 2N hydrochloric acid, and powdery phthalimide (7.4 g, 0.05 mol) was slowly added thereto with stirring. Then, the mixture was stirred at 97° C. for 3 hours to obtain an aqueous solution containing phthalic acid. Phthalic acid was recovered by condensing and filtering the aqueous solution. Then, to a flask, were added the phthalic acid, 100 mL of pyridine and 0.5 g of sulfuric acid, and stirred for 3 hours at 100° C. with distilling off water formed by reaction to obtain a mixture containing phthalic anhydride. Hydroxylamine hydrochloride $NH_2OH \cdot HCl$ (6.9 g, 0.1 mol) was added to the mixture and stirred at 50° C. for 3 hour to form N-hydroxyphthalimide (5.74 g, yield 70%).

Example F4

To a flask was added 50 mL of 1N sodium hydroxide aqueous solution, and powdery N-cyclohexyloxyphthalimide (4.9 g, 20 mmol) was slowly added thereto with stirring. The mixture was stirred at 97° C. for 5 hours to obtain an aqueous solution containing sodium salt of phthalic acid. To the aqueous solution was added diluted hydrochloric acid to convert into phthalic acid, and phthalic acid was recovered by condensation and filtration. To a flask were added the phthalic acid, 50 mL of pyridine and 0.05 g of sulfuric acid and stirred at 95° C. for 4 hours to obtain a mixture containing phthalic anhydride. Hydroxylamine hydrochloride $NH_2OH \cdot HCl$ (2.8 g, 40 mmol) was added to the mixture, stirred at 50° C. for 3 hours to form N-hydroxyphthalimide (2.6 g, yield 81%).

Example F5

A mixture of 1500 g (17.82 mol) of cyclohexane, 3.16 g (0.019 mol) of N-hydroxyphthalimide, and 0.045 g (0.18 mmol) of cobalt acetate was reacted at 160° C. and 40 kgf/cm$^2$ (3.92 MPa) in atmosphere of oxygen for 2 hours to obtain a mixture containing 1334 g (15.84 mol) of cyclohexane, 83.89 g (0.84 mol) of cyclohexanol, 59.47 g (0.61 mol) of cyclohexanone, 1.77 g (0.012 mol) of phthalimide, and 1.30 g (0.005 mol) of N-cyclohexyloxyphthalimide. From the reaction mixture, cyclohexane was distilled off, 2N (2 mol/L) of sodium hydroxide aqueous solution (30 mL) was added thereto, completely mixed for 2 hours at 97° C. and stood for 1 hour to be liquid-separated into an aqueous layer and an organic layer. Phthalimide and N-cyclohexyloxyphthalimide were distributed into the aqueous layer by converting into sodium salt of phthalic acid. To the aqueous layer was added diluted hydrochloric acid to convert into phthalic acid, and phthalic acid was recovered by condensation and filtration. After hydroxylamine hydrochloride $NH_2OH \cdot HCl$ (1.39 g, 40 mmol) was dissolved in 50 mL of pyridine, the recovered phthalic acid was added thereto, and stirred at 97° C. for 4 hours. The mixture was condensed, filtrated and washed with hexane to form N-hydroxyphthalimide (2.05 g, 0.013 mol). The regeneration ratio of N-hydroxyphthalimide (a ratio of N-hydroxyphthalimide regenerated relative to N-hydroxyphthalimide used in the reaction) was 65%.

Example F6

A mixture of 1500 g (17.82 mol) of cyclohexane, 3.16 g (0.019 mol) of N-hydroxyphthalimide, and 0.045 g (0.18 mmol) of cobalt acetate was reacted at 160° C. and 40 kgf/cm$^2$ (3.92 MPa) in atmosphere of oxygen for 2 hours to obtain a mixture containing 1275 g (15.13 mol) of cyclohexane, 130.8 g (1.31 mol) of cyclohexanol, 89.69 g (0.92 mol) of cyclohexanone, 2.07 g (0.014 mol) of phthalimide, and 0.78 g (0.003 mol) of N-cyclohexyloxyphthalimide. From the reaction mixture, cyclohexane was distilled off, 2N (2 mol/L) of sodium hydroxide aqueous solution (30 mL) was added thereto, mixed completely for 2 hours at 97° C. and allowed to stand for 1 hour to be liquid-separated into an aqueous layer and an organic layer. Phthalimide and N-cyclohexyloxyphthalimide were distributed into the aqueous layer by converting into sodium salt of phthalic acid. To the aqueous layer was added diluted hydrochloric acid to convert into phthalic acid, and phthalic acid was recovered by condensation and filtration. To a flask were added the phthalic acid, 50 mL of pyridine and 0.05 g of sulfuric acid and stirred at 95° C. for 4 hours to obtain a mixture containing phthalic anhydride. Hydroxylamine hydrochloride NH$_2$OH.HCl (2.8 g, 40 mmol) was added to the mixture and stirred at 50° C. for 3 hours. The mixture was condensed, filtrated and washed with cyclohexane to 2.21 g (0.013 mol) of N-hydroxyphthalimide. The regeneration ratio of N-hydroxyphthalimide (a ratio of N-hydroxyphthalimide regenerated relative to N-hydroxyphthalimide used in the reaction) was 70%.

The invention claimed is:

1. A process for separating a reaction product and an imide compound having an imide unit represented by the following formula (1):

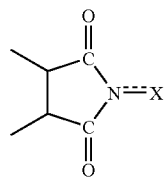

wherein X represents an oxygen atom, a hydroxyl group, or an acyloxy group, from a reaction mixture obtained by a reaction of a substrate selected from the group consisting of a hydrocarbon, an alcohol corresponding to the hydrocarbon, an aldehyde corresponding to the hydrocarbon, a ketone corresponding to the hydrocarbon, an amine, a heterocyclic compound, a thiol, a sulfide, and an amide, in the presence of the imide compound, wherein the reaction mixture is obtained by (i) oxidizing the substrate with oxygen, (ii) carboxylating the substrate with oxygen and carbon monoxide, (iii) nitrating the substrate with a nitrogen oxide, (iv) sulfonating the substrate with a sulfur oxide, (v) acylating the substrate with a vicinal-dicarbonyl compound, or (vi) radically coupling the substrate with a compound which is radically formable of a carbon-carbon bond, which process comprises separating said reaction product and said imide compound from said reaction mixture by solvent-crystallizing the imide compound from said reaction mixture with water or a mixture of water and at least one solvent selected from the group consisting of a hydrocarbon and a chain ether, or, when the reaction mixture is obtained by an oxidation reaction of a monocyclic C$_{4-16}$cycloalkane substrate, with at least one solvent selected from the group consisting of a hydrocarbon and a chain ether.

2. The process of claim 1, wherein separation of said reaction product is by a solvent-crystallization step in which the hydrocarbon employed as a solvent is an aliphatic hydrocarbon having 4 to 16 carbon atoms or an alicyclic hydrocarbon having 4 to 16 carbon atoms, and the chain ether employed as a solvent is a di-C$_{1-6}$alkyl ether or a C$_{1-6}$alkyl C$_{6-10}$aryl ether.

3. The process of claim 2, wherein the imide compound is an aromatic imide compound, and the reaction product is an oxidation reaction product of an alicyclic hydrocarbon or an alicyclic alcohol and is soluble in the solvent for crystallization in the solvent-crystallization step.

4. The process of claim 1, wherein the imide compound is an oxidation catalyst for oxidizing the substrate, and the reaction product is an oxidation reaction product corresponding to the substrate.

* * * * *